US011249079B2

(12) United States Patent
Chilkoti et al.

(10) Patent No.: US 11,249,079 B2
(45) Date of Patent: *Feb. 15, 2022

(54) DETECTION DEVICES AND RELATED METHODS OF USE

(71) Applicant: Sentilus Holdco, LLC, Norcross, GA (US)

(72) Inventors: Ashutosh Chilkoti, Durham, NC (US); Angus Hucknall, Durham, NC (US)

(73) Assignee: SENTILUS HOLDCO, LLC, Norcross, GA (US)

( * ) Notice: Subject to any disclaimer, the term of this patent is extended or adjusted under 35 U.S.C. 154(b) by 434 days.

This patent is subject to a terminal disclaimer.

(21) Appl. No.: 16/387,010

(22) Filed: Apr. 17, 2019

(65) Prior Publication Data
US 2019/0391141 A1 Dec. 26, 2019

Related U.S. Application Data

(63) Continuation of application No. 15/336,097, filed on Oct. 27, 2016, now Pat. No. 10,302,636, which is a continuation of application No. 13/698,383, filed as application No. PCT/US2011/036811 on May 17, 2011, now Pat. No. 9,482,664.

(Continued)

(51) Int. Cl.
| G01N 33/543 | (2006.01) |
| A61B 5/15 | (2006.01) |
| A61B 5/151 | (2006.01) |
| A61B 5/157 | (2006.01) |

(52) U.S. Cl.
CPC ....... *G01N 33/54366* (2013.01); *A61B 5/157* (2013.01); *A61B 5/150022* (2013.01); *A61B 5/15142* (2013.01); *A61B 5/150358* (2013.01); *A61B 5/150755* (2013.01); *G01N 33/54393* (2013.01); *A61B 5/1411* (2013.01); *A61B 2562/0295* (2013.01)

(58) Field of Classification Search
CPC ........ G01N 33/54366; G01N 33/54393; A61B 5/150022; A61B 5/150358; A61B 5/150755; A61B 5/15142; A61B 5/157; A61B 2562/0295; A61B 5/1411
See application file for complete search history.

(56) References Cited

U.S. PATENT DOCUMENTS

| 4,822,135 A | 4/1989 | Seaver |
| 4,844,613 A | 7/1989 | Batchelder et al. |

(Continued)

FOREIGN PATENT DOCUMENTS

| EP | 1912067 A1 * | 4/2008 | ........... C12Q 1/6837 |
| EP | 1912067 A1 | 4/2008 | |
| WO | WO 98/35232 A2 | 8/1998 | |

OTHER PUBLICATIONS

Angus et al, "Simple Fabrication of Antibody Microarrays on Nonfouling Polymer Brushes with Femtomolar Sensitivity for Protein Analytes in Serum and Blood", Advanced Materials, vol. 21, No. 19, May 18, 2009 (May 18, 2009), pp. 1968-1971 (Year: 2009).*

(Continued)

*Primary Examiner* — Dennis White
(74) *Attorney, Agent, or Firm* — Cozen O'Connor

(57) ABSTRACT

Disclosed are devices and methods for detecting analytes from a sample.

20 Claims, 14 Drawing Sheets

Related U.S. Application Data

(60) Provisional application No. 61/345,259, filed on May 17, 2010.

(56) References Cited

U.S. PATENT DOCUMENTS

| | | | |
|---|---|---|---|
| 5,288,514 | A | 2/1994 | Ellman |
| 5,313,264 | A | 5/1994 | Ivarsson et al. |
| 5,413,690 | A | 5/1995 | Kost et al. |
| 5,415,842 | A | 5/1995 | Maule |
| 5,445,934 | A | 8/1995 | Fodor et al. |
| 5,485,277 | A | 1/1996 | Foster |
| 5,496,701 | A | 3/1996 | Pollard-Knight |
| 5,621,209 | A | 4/1997 | Purser |
| 5,624,711 | A | 4/1997 | Sundberg et al. |
| 5,625,455 | A | 4/1997 | Nash et al. |
| 5,777,372 | A | 7/1998 | Kobashi |
| 5,815,278 | A | 9/1998 | Johnston et al. |
| 5,822,073 | A | 10/1998 | Yee et al. |
| 5,846,842 | A | 12/1998 | Herron et al. |
| 5,991,048 | A | 11/1999 | Karlson et al. |
| 6,413,587 | B1 | 7/2002 | Hawker et al. |
| 6,423,055 | B1 | 7/2002 | Farr et al. |
| 6,423,465 | B1 | 7/2002 | Hawker et al. |
| 6,444,254 | B1 | 9/2002 | Chilkoti et al. |
| 6,512,060 | B1 | 1/2003 | Matyjaszewski et al. |
| 6,521,209 | B1 | 2/2003 | Meade et al. |
| 6,541,580 | B1 | 4/2003 | Matyjaszewski et al. |
| 6,570,657 | B1 | 5/2003 | Hoppe et al. |
| 6,573,107 | B1 | 6/2003 | Bowen et al. |
| 6,579,721 | B1 | 6/2003 | Natan et al. |
| 6,649,138 | B2 | 11/2003 | Adams et al. |
| 6,780,582 | B1* | 8/2004 | Wagner ............... B82Y 5/00 506/32 |
| 2002/0128234 | A1 | 9/2002 | Hubbell |
| 2003/0104506 | A1* | 6/2003 | Durst ............... G01N 33/558 435/7.92 |
| 2003/0108879 | A1 | 6/2003 | Klaerner et al. |
| 2003/0185741 | A1 | 10/2003 | Matyjaszewski et al. |
| 2007/0072220 | A1* | 3/2007 | Chilkoti ............ C12Q 2525/313 435/6.12 |
| 2009/0247424 | A1* | 10/2009 | Chilkoti ............ G01N 33/54366 506/9 |
| 2009/0277805 | A1 | 11/2009 | Amemiya et al. |
| 2010/0099579 | A1* | 4/2010 | Chilkoti ............... B01J 19/0046 506/16 |

OTHER PUBLICATIONS

Peng et al "Comparison of Hydroxylated Print Additives on Antibody Microarray Performance", Journal of Proteome Research, vol. 5, No. 11, Nov. 1, 2006 (Nov. 1, 2006), pp. 2956-2965 (Year: 2006).*

International Search Report corresponding to International Application No. PCT/US2011/036811 dated Aug. 12, 2011.

Hucknall et al., "Simple Fabrication of Antibody Microarrays on Nonfouling Polymer Brushes with Femtomolar Sensitivity for Protein Analytes in Serum and Blood", (Advance Materials, 2009,21: 1968-1971).

Tirosh et al., "Hydration of Polyethylene Glycol-Grafted Liposomes", (Biophysical Journal, 1998, 74:1371-1379).

Lu et al., "Fabrication and Characterization of Paper-Based Microfluidics Prepared in Nitrocellulose Membrane By Wax Printing", (Anal. Chem., 2010, 82:329-335).

Jinhua Dai et al., "High-Capacity Binding of Proteins by Poly(Acrylic Acid) Brushes and Their Derivatives", Langmuir, vol. 22, pp. 4274-4281 (2006).

Extended European Search Report issued in European Application No. 11784092.6, dated Sep. 18, 2014, 6 pages.

Wu, et al., "Comparison of Hydroxylated Print Additives on Antibody Microarray Performance", Journal of Proteome Research, vol. 5, No. 11, pp. 2956-2965, 2006.

* cited by examiner

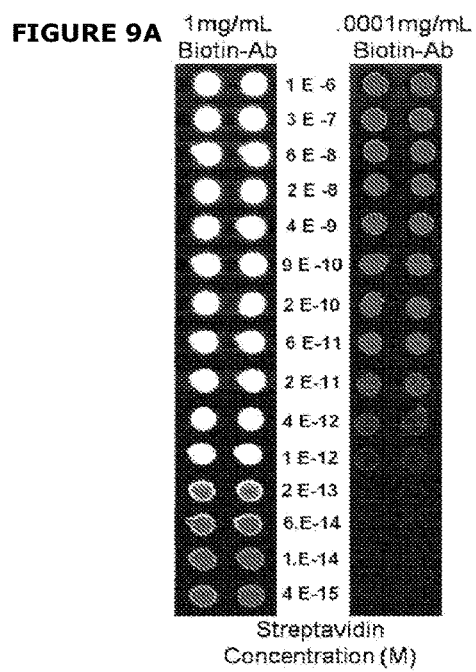
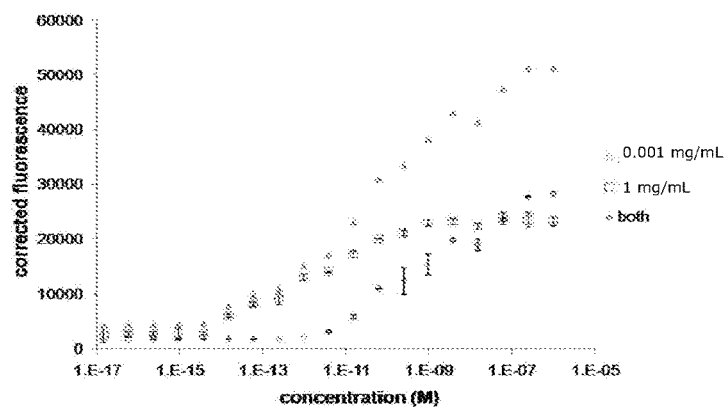
FIGURE 9A
FIGURE 9B Dose Response Streptavidin

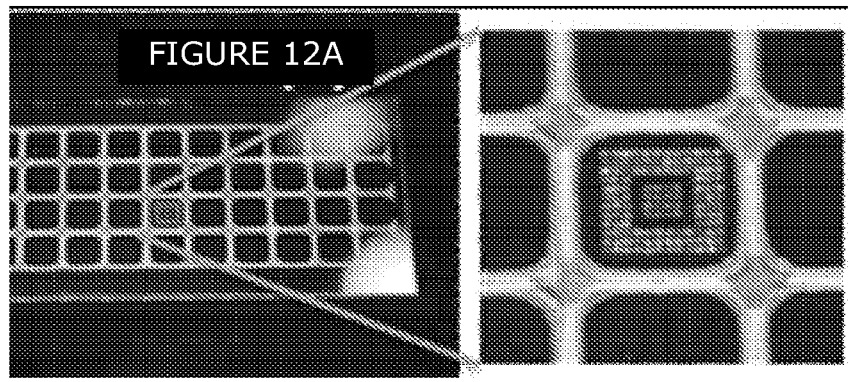
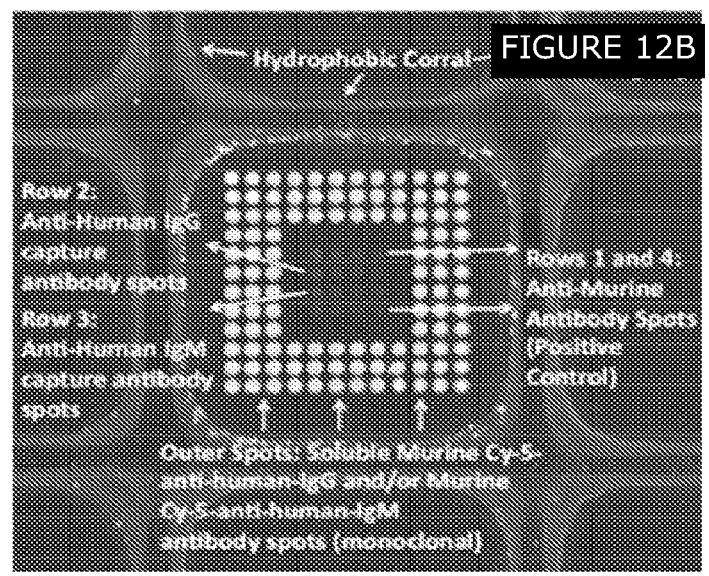

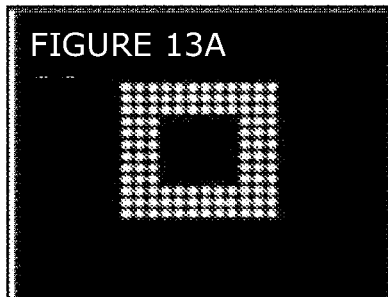
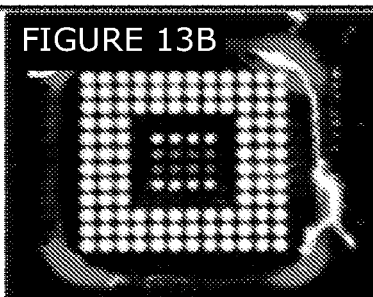
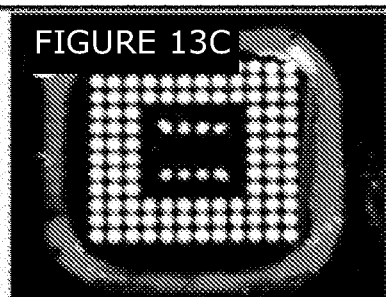
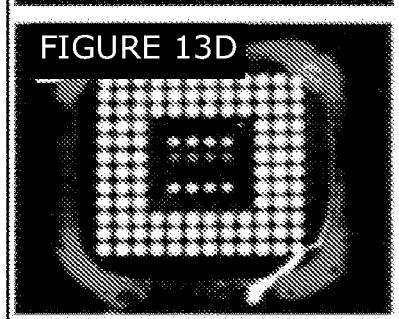
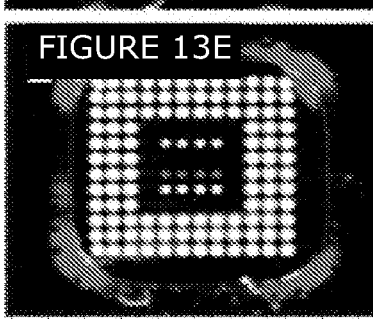
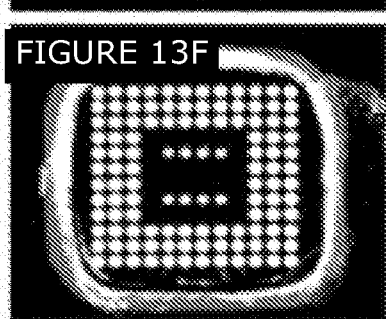

DETECTION DEVICES AND RELATED METHODS OF USE

CROSS-REFERENCE TO RELATED APPLICATIONS

This application is a continuation of U.S. patent application Ser. No. 15/336,097, filed Oct. 27, 2016, which is a continuation of U.S. application Ser. No. 13/698,383, filed Feb. 28, 2013, issued as U.S. Pat. No. 9,482,664, which is a 35 U.S.C. § 371 national stage application of PCT Application No. PCT/US2011/036811, filed May 17, 2011, which claims priority to U.S. Provisional Patent Application No. 61/345,259, filed on May 17, 2010, the disclosures of each of which are incorporated herein by reference in their entireties.

BACKGROUND

Microarrays based on nucleic acid technology are well established tools for applications such as genetic analysis and diagnostics based on gene expression patterns. Other microarray platform technologies such as protein (antibody) arrays, and assays based on analysis of complex biological samples (cell preparations, whole blood, etc.) are not as well developed in light of technical challenges that are not necessarily found in nucleic acid arrays. Such challenges include complicated and/or multi-step sample processing, inconsistent binding activity or lack of stability of non-nucleotide capture agents, variation in binding function based on assay conditions (e.g., solubility, pH, etc.), and non-specific binding associations (e.g., biomolecules to microarray surface). Such non-specific binding can hamper signal detection as it generates high background signal (noise). Further, microarray technologies typically employ additional preparative steps, such as steps that involve sample fractionation or purification, and/or the binding or association of a detectable group with an analyte prior or subsequent to its binding to a capture agent.

Accordingly, devices and methods that enable the detection of one or more analytes in a single sample with minimal or no sample pre-processing steps, that have a low propensity for non-specific association between sample components and the substrate, and that employ a single or small number of assay steps can provide advantages over existing devices and detection methods.

SUMMARY

In one aspect, the disclosure provides a device comprising: a substrate comprising a surface; a non-fouling polymer layer on the surface; at least one capture region on the polymer layer, comprising at least one capture agent; and at least one labile region on the polymer layer, comprising at least one detection agent and an excipient; wherein the capture region and the labile region are spatially separated.

In another aspect, the disclosure provides a method of manufacturing a device described herein, the method comprising: providing a substrate comprising a surface; forming a non-fouling polymer layer on the surface; printing at least one capture agent onto the polymer layer; and printing at least one detection agent and at least one excipient onto the polymer layer; wherein the capture agent is printed onto the polymer layer in a region that is spatially separated from the detection agent and excipient.

In another aspect, the disclosure provides a method of screening for a disease or a disorder in a subject comprising: obtaining a sample from the subject; contacting the sample with a device described herein for a time sufficient to allow the detection agent in the labile region to solubilize; and detecting the presence of the disease or disorder, wherein a detectable, wherein a detectable signal on at least one capture region on the device indicates the presence of disease or disorder in the subject.

In another aspect, the disclosure provides a diagnostic assay for identifying a disease, disorder, or biological state in a subject comprising: obtaining a sample from the subject; contacting the sample with a device described herein for a time sufficient to allow the detection agent in the labile region to solubilize; detecting the presence of the disease, disorder, and/or biological state in the subject, wherein a detectable signal on at least one capture region on the device indicates the presence of the disease, disorder, and/or biological state in the subject.

The disclosure relates to other aspects and embodiments that will become apparent from the following description and accompanying figures.

BRIEF DESCRIPTION OF THE DRAWINGS

In FIGS. 8B-D, the ordinate shows the average background subtracted fluorescence intensity in spots and the X-axis shows the analyte concentration in solution. Error bars represent one standard deviation.

FIG. 9A depicts biotinylated antibody (b-Ab) spots after exposure to a dilution series of streptavidin-Cy5, printed from 1 mg/mL b-Ab (left) and 0.0001 mg/mL (right) b-Ab solutions; FIG. 9B depicts dose response curves of spots to the dilution series of strep tavidin-Cy5.

FIGS. 12A and B depict images of a glass slide with POEGMA brush stamped with grid of wax. FIG. 12A shows image illustrating an antibody array spotted in the center of a single wax corral. FIG. 12A shows magnified fluorescence image of inner 4×4 antibody array surrounded by spots containing soluble fluorescent detection reagents.

FIGS. 13A to 13F depict results of an exemplary assay for IgG and IgM. FIG. 13A) Printed assay chip. FIG. 13B) Co-printed detection antibodies for IgG and IgM co-printed as the labile detection spots. FIG. 13C) Negative control in which the chip was incubated with PBS. FIG. 13D) Assay in which only Cy5-anti-IgG detection agent was printed in the labile spots. FIG. 13E) Assay in which only Cy5-anti-IgM detection agent was printed in the labile spots. FIG. 13F) Negative control in which the chip was incubated with chicken blood.

DETAILED DESCRIPTION

Figure 1:
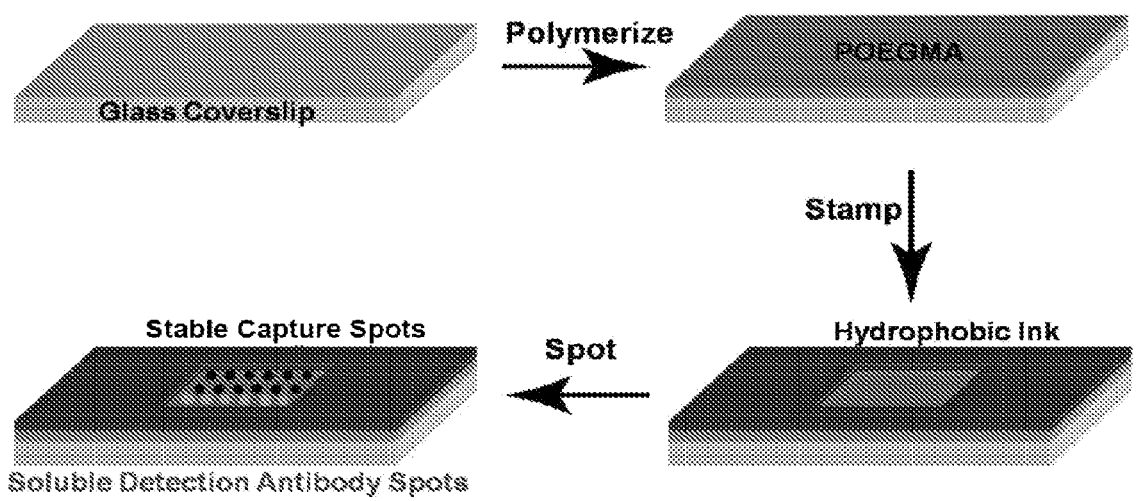
FIG. 1 depicts an exemplary disposable chip which has been coated with POEGMA, stamped with a hydrophobic ink, and printed with "capture spots" and "labile spots".

The disclosure is not limited in its application to the details of construction and the arrangement of components set forth in the following description or illustrated in the drawings. The objects described in the disclosure are capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items. For the purposes of promoting an understanding of the principles of the disclosure, reference is made to various aspects and related embodiments with illustrative language used to describe the same.

Articles "a," "an," and "the" are used herein to refer to one or to more than one (i.e. at least one) of the grammatical object of the article. By way of example, "an element" means at least one element and can include more than one element. Similarly, reference to "a cell" includes a plurality of cells, and in some embodiments, can include a tissue and/or an organ. Similarly, the term "and/or" as used herein should be understood to include any single element recited within the relevant phrase, as well as any combination of two or more elements, including all elements.

Unless otherwise defined, all technical terms used herein have the same meaning as commonly understood by one of ordinary skill in the art to which this disclosure belongs.

Definitions

While the following terms are believed to be well understood by one of ordinary skill in the art, the following definitions are set forth to facilitate explanation of the disclosed subject matter. Although any methods, devices, and materials similar or equivalent to those described herein can be used in the practice or testing of the disclosed subject matter, representative methods, devices and materials are now described.

As used herein, the term "sample" or "biological sample" relates to any material that is taken from its native or natural state, so as to facilitate any desirable manipulation or further processing and/or modification. A sample or a biological sample can comprise a cell, a tissue, a fluid (e.g., a biological fluid), a protein (e.g., antibody, enzyme, soluble protein, insoluble protein), a polynucleotide (e.g., RNA, DNA), a membrane preparation, and the like, that can optionally be further isolated and/or purified from its native or natural state. A "biological fluid" refers to any fluid originating from a biological organism. Exemplary biological fluids include, but are not limited to, blood, serum, plasma, lymph fluid, bile fluid, urine, saliva, mucus, sputum, tears, cerebrospinal fluid (CSF), bronchioalveolar lavage, nasopharyngeal lavage, rectal lavage, vaginal lavage, colonic lavage, nasal lavage, throat lavage, synovial fluid, semen, ascites fluid, pus, maternal milk, ear fluid, sweat, and amniotic fluid. A biological fluid may be in its natural state or in a modified state by the addition of components such as reagents, or removal of one or more natural constituents (e.g., blood plasma).

As used herein, the term "biomarker" refers to a substance that is associated with a biological state or a biological process, such as a disease state or a diagnostic or prognostic indicator of a disease or disorder (e.g., an indicator identifying the likelihood of the existence or later development of a disease or disorder). The presence or absence of a biomarker, or the increase or decrease in the concentration of a biomarker, may be associated with and/or be indicative of a particular state or process. Biomarkers may include, but are not limited to, cells or cellular components (e.g., a viral cell, a bacterial cell, a fungal cell, a cancer cell, etc.), small molecules, lipids, carbohydrates, nucleic acids, peptides, proteins, enzymes, antigens and antibodies. A biomarker may be derived from an infectious agent, such as a bacterium, fungus or virus, or may be an endogenous molecule that is found in greater or lesser abundance in a subject suffering from a disease or disorder as compared to a healthy individual (e.g., an increase or decrease in expression of a gene or gene product).

As used herein, the term "detection moiety" is any moiety or compound that is detectable by methods including, but not limited to, spectroscopic, photochemical, biochemical, immunochemical, chemical, electrochemical, radioactivity, and other physical means. A detection moiety may be detectable indirectly; for example, the detection moiety may be a moiety or compound that is a member of a specific binding pair, wherein the second member of the binding pair includes a detection moiety that can be detected directly. A non-limiting and known example of such a detection moiety is biotin, which may bind to avidin or streptavidin comprising a detection moiety such as a fluorophore. Exemplary detection moieties include, but are not limited to, fluorophores, chromophores, radiolabels, polynucleotides, small molecules, enzymes, nanoparticles, and upconverters.

As used herein, the term "infectious disease" (herein abbreviated as ID) refers to those diseases that are caused by infectious agents including, but not limited to, microbes such as, for example, viruses, bacteria, archaea, planaria, amoeba, and fungi.

The term "polymer," as used herein, is given its ordinary meaning as used in the art, i.e., a molecular structure featuring one or more repeat units (monomers), connected by covalent bonds. The repeat units may all be identical, or in some cases, there may be more than one type of repeat unit present within the polymer. The term polymer is intended to encompass any type of polymer, including homopolymers, copolymers (e.g., random copolymers, block copolymers, graft copolymers, etc.), and blends, combinations and mixtures thereof. Polymers may be linear, branched, star-shaped, etc.

As used herein, the term "region" refers to a defined area on the surface of a material. A region can be identified and bounded by a distinct interface between two materials having different compositions.

"Specific binding pair" as used herein refers to two molecules that exhibit specific binding to one another, or increased binding to one another relative to other molecules. A specific binding pair can exhibit functional binding activity such as, for example, a receptor and a ligand (such as a drug, protein, or carbohydrate), an antibody and an antigen, etc.; or structural binding activity such as, for example, protein/peptide and protein/peptide; protein/peptide and nucleic acid; and nucleotide and nucleotide etc. Typically, one member of the binding pair may serve as a capture agent in the devices described herein, and the capture agent may bind to the second member of the binding pair, which can be present as an analyte in a sample such as a biological fluid. "Analyte" as used herein may be any second member of a specific binding pair, as described above. Typically the analyte is a constituent of, or found in, a sample such as a biological fluid. The analyte can be a biomarker as described above.

As used herein, the term "subject" and "patient" are used interchangeably and refer to both human and nonhuman animals. The term "nonhuman animals" includes all vertebrates, e.g., mammals and non-mammals, including but not limited to nonhuman primates, sheep, dog, cat, horse, cow, chickens, amphibians, reptiles, and the like. In certain embodiments, the subject is a human patient.

In a general sense, the disclosure relates to a device comprising a substrate comprising a surface; a non-fouling polymer layer on the surface; at least one capture region on the polymer layer, comprising at least one capture agent; and at least one labile region on the polymer layer, comprising at least one detection agent and an excipient; wherein the capture region and the labile region are spatially separated. The disclosure also provides for methods, assays, and kits that comprise the device. The non-fouling polymer layer can provide for the reduction of non-specific binding between sample components and the substrate and/or the polymer layer. The labile region on the polymer layer can allow for simplified methods and assays by reducing the necessary steps involved in a typical assay such as, for example, merely contacting the surface of the device with a sample and subsequently detecting any signal from the capture region, while still providing for highly sensitive detection limits. The devices and associated methods are highly adaptable to a number of settings, including research and clinical laboratories as well as large-scale point of care assays.

Substrates

A variety of different types of substrates can be used in accordance with the disclosure.

In embodiments, the substrate comprises a surface that allows for the application of a polymer layer. In some embodiments, the substrate is a label-free optical or mass detector (e.g., a surface plasmon resonance energy detector, an optical wave guide, an ellipsometry detector, etc.) and the surface of the substrate is a sensing surface (e.g., a surface portion that would be in contact with a biological fluid). Examples of such devices include but are not limited to those described in U.S. Pat. Nos. 6,579,721; 6,573,107; 6,570,657; 6,423,055; 5,991,048; 5,822,073; 5,815,278; 5,625,455; 5,485,277; 5,415,842; 4,844,613; and 4,822,135.

In other embodiments, the substrate is a biosensor, an assay plate, or the like. For example, the substrate may be an optical biosensor, such as those described in U.S. Pat. Nos. 5,313,264, 5,846,842, 5,496,701, etc. The substrate may also be a potentiometric or electrochemical biosensor, such as described in U.S. Pat. No. 5,413,690, or PCT Application WO98/35232. The substrate may be a diamond film biosensor, such as described in U.S. Pat. No. 5,777,372. Accordingly, the substrate may be organic or inorganic; may be metal (e.g., copper or silver) or non-metal; may be a polymer or nonpolymer; may be conducting, semiconducting or nonconducting (insulating); may be reflecting or nonreflecting; may be porous or nonporous; etc. For example, the substrate may comprise polyethylene, polytetrafluoroethylene, polystyrene, polyethylene terephthalate, polycarbonate, gold, silicon, silicon oxide, silicon oxynitride, indium, tantalum oxide, niobium oxide, titanium, titanium oxide, platinum, iridium, indium tin oxide, diamond or diamond-like film, etc.

The substrate may be a substrate suitable for "chip-based" and "pin-based" combinatorial chemistry techniques. All can be prepared in accordance with known techniques. See, e.g., U.S. Pat. Nos. 5,445,934, 5,288,514 and 5,624,711.

Substrates as described above can be formed of any suitable material, including but not limited to a material selected from the group consisting of metals, metal oxides, alloys, semiconductors, polymers (such as organic polymers in any suitable form including woven, nonwoven, molded, extruded, cast, etc.), silicon, silicon oxide, ceramics, glass, and composites thereof.

Polymers used to form substrates as described herein may be any suitable polymer, including but not limited to: poly(ethylene) (PE), poly(propylene) (PP), cis and trans isomers of poly(butadiene) (PB), cis and trans isomers of poly(isoprene), poly(ethylene terephthalate) (PET), polystyrene (PS), polycarbonate (PC), poly(epsilon-caprolactone) (PECL or PCL), poly(methyl methacrylate) (PMMA) and its homologs, poly(methyl acrylate) and its homologs, poly (lactic acid) (PLA), poly(glycolic acid), polyorthoesters, poly(anhydrides), nylon, polyimides, polydimethylsiloxane (PDMS), polybutadiene (PB), polyvinyl alcohol (PVA), polyacrylamide and its homologs such as poly(N-isopropyl acrylamide), fluorinated polyacrylate (PFOA), poly(ethylene-butylene) (PEB), poly(styrene-acrylonitrile) (SAN), polytetrafluoroethylene (PTFE) and its derivatives, polyolefin plastomers, and combinations and copolymers thereof, etc.

The substrate may optionally have an additional layer such as a gold or an oxide layer formed on the surface of the substrate, for example, to facilitate the deposition of a polymer layer or a linking layer, as discussed further below.

Linking Layer

Depending on the choice of substrate and polymer, a linking layer may optionally be included between the substrate and the polymer layer. For example, a linking layer may be formed from a compound comprising an anchor group coupled (e.g., covalently coupled) to an initiator (e.g., directly coupled or coupled through an intermediate linking group). The choice of anchor group will depend upon the substrate on which the linking layer is formed, and the choice of initiator will depend upon the particular reaction used to form the non-fouling polymer as discussed in greater detail below.

The anchoring group may covalently or non-covalently couple the compound or linking layer to the surface of the substrate. Non-covalent coupling may be by any suitable secondary interaction, including but not limited to hydrophobic interactions, hydrogen bonding, van der Waals forces, ionic bonds, metal-ligand interactions, etc.

Examples of substrate materials and corresponding anchoring groups include, for example, gold, silver, copper, cadmium, zinc, palladium, platinum, mercury, lead, iron, chromium, manganese, tungsten, and any alloys thereof with sulfur-containing functional groups such as thiols, sulfides, disulfides (e.g., —SR or —SSR where R is H, alkyl such as lower alkyl, or aryl), and the like; doped or undoped silicon with silanes and chlorosilanes (e.g., —SiR$_2$Cl wherein R is H, alkyl such as lower alkyl, or aryl); metal oxides such as silica, alumina, quartz, glass, and the like with carboxylic acids as anchoring groups; platinum and palladium with nitrites and isonitriles; and copper with hydroxamic acids. Additional suitable functional groups suitable as the anchoring group include benzophenones, acid chlorides, anhydrides, epoxides, sulfonyl groups, phosphoryl groups, hydroxyl groups, phosphonates, phosphonic acids, amino acid groups, amides, and the like. See, e.g., U.S. Pat. No. 6,413,587.

Any suitable initiator may be incorporated into the anchoring group by introduction of a covalent bond at a location non-critical for the activity of the initiator. Examples of such initiators include, but are not limited to, bromoisobutyrate, polymethyl methacrylate-Cl, polystyrene-Cl, AIBN, 2-bromoisobutyrate, chlorobenzene, hexabromomethyl benzene, hexachloromethyl benzene, dibromoxylene, methyl bromoproprionate. Additional examples of initiators include those initiators described in U.S. Pat. No. 6,413,587 (e.g., at columns 10-11 thereof) and those initiators described in U.S. Pat. No. 6,541,580.

As noted above, a linking group or "spacer" may be inserted between the anchoring group and initiator. The linker may be polar, nonpolar, positively charged, negatively charged or uncharged, and may be, for example, saturated or unsaturated, linear or branched alkylene, heteroalkylene, aralkylene, alkarylene, or other hydrocarbylene, such as halogenated hydrocarbylene, particularly fluorinated hydrocarbylene. Suitable linkers are saturated alkylene groups of 3 to 20 carbon atoms, i.e., —(CH$_2$)$_n$—, where n is an integer of 3 to 20 inclusive. See, e.g., U.S. Pat. No. 6,413,587. Another suitable embodiment of the linker is an oligoethyleneglycol of 3 to 20 units, i.e., —(CH$_2$CH$_2$O)$_n$— where n is an integer of 3 to 20 inclusive.

The anchoring layer may be deposited by any suitable technique. It may be deposited as a self-assembled monolayer. It may be created by modification of the substrate by chemical reaction (see, e.g., U.S. Pat. No. 6,444,254) or by reactive plasma etching or corona discharge treatment. Tt may be deposited by a plasma deposition process. Tt may be deposited by spin coating or dip coating. It may be deposited by spray painting. It may also be deposited by deposition, printing, stamping, etc. It may be deposited as a continuous layer or as a discontinuous (e.g., patterned) layer.

In some embodiments, the substrate may be glass, silicon oxide or other inorganic or semiconductor material (e.g., silicon oxide, silicon nitride) or compound semiconductors (e.g., gallium arsenide, and indium gallium arsenide) commonly used for microarray production. In some embodiments, the substrate can be a microtiter (microwell) plate.

In some embodiments, the anchoring group may be a silane or chlorosilane (e.g., —SiR$_2$Cl wherein R is H, alkyl such as lower alkyl, or aryl).

In some embodiments, the linking layer is formed on the substrate in two separate steps. For example, in a first step, an anchoring layer of alkylsilane or alkanethiol may be deposited on a surface such as silicon dioxide or glass or gold, and presents a terminal reactive functional group (e.g., amine). Subsequently, a bifunctional molecule, which comprises a first functional group reactive towards the terminal group presented by the first linking layer may be reacted with the first linking layer deposited in the first step. The second functional group of the bifunctional molecule contains a moiety group that acts as an initiator for the polymerization of the polymer layer, such as an ATRP initiator.

Polymer Layer

The polymer layers of the devices described herein exhibit non-fouling properties. Non-fouling, as used herein with respect to the polymer layer, relates to the inhibition (e.g., reduction or prevention) of growth of an organism as well as to non-specific or adventitious binding interactions between the polymer and an organism or biomolecule (e.g., cell, protein, nucleotide, etc.). The non-fouling property of the polymer can be introduced by any suitable method such as, for example, incorporation of a non-fouling (or alternatively, antifouling) agent or by the structure/architecture of the polymer itself. Non-fouling agents are known in the art and can be selected by one of skill depending on the particular use of device, or on the availability of the non-fouling agent. Non-limiting examples include organic and inorganic compounds having biocidal activity, as well as compounds that can be incorporated with or bound to the polymer layer that reduce or inhibit non-specific binding interaction of a biomolecule (e.g., cell, protein, nucleotide, carbohydrate/lipid) with the polymer upon contact.

Some embodiments provide a polymer layer having a structure or architecture that provides a non-fouling property. In some embodiments the polymer may suitably include brush polymers, which are, in general, formed by the polymerization of monomeric core groups having one or more groups that function to inhibit binding of a biomolecule (e.g., cell, protein, nucleotide, carbohydrate/lipid) coupled thereto. Suitably, the monomeric core group can be coupled to a protein-resistant head group.

Polymer layers may suitably be formed using radical polymerization techniques, such as catalytic chain transfer polymerization, iniferter mediated polymerization (e.g., photoiniferter mediated polymerization), free radical polymerization, stable free radical mediated polymerization (SFRP), atom transfer radical polymerization (ATRP), and reversible addition-fragmentation chain transfer (RAFT) polymerization.

For example, free radical polymerization of monomers to form brush polymers can be carried out in accordance with known techniques, such as described in U.S. Pat. Nos. 6,423,465, 6,413,587 and 6,649,138, U.S. Patent Application No. 2003/0108879, and variations thereof which will be apparent to those skilled in the art.

Atom transfer radical polymerization of monomers to form brush polymers can also be carried out in accordance with known techniques, such as described in U.S. Pat. Nos. 6,541,580 and 6,512,060, U.S. Patent Application No. 2003/0185741, and variations thereof which will be apparent to those skilled in the art.

Any suitable core vinyl monomer polymerizable by the processes discussed above can be used, including but not limited to styrenes, acrylonitriles, acetates, acrylates, methacrylates, acrylamides, methacrylamides, vinyl alcohols, vinyl acids, and combinations thereof.

In some embodiments, the polymer layer is formed by surface-initiated ATRP (SI-ATRP) of oligo(ethylene glycol) methyl methacrylate (OEGMA) to form a poly(OEGMA) (POEGMA) film. In an embodiment, the polymer layer is a functionalized POEGMA film prepared by copolymerization of a methacrylate and methoxy terminated OEGMA. Suitably, the POEGMA polymer may be formed in a single step.

In general, the brush molecules formed by the processes described herein (or other processes either known in the art or which will be apparent to those skilled in the art), may be from 2 or 5 up to 100 or 200 nanometers in length, or more, and may be deposited on the surface portion at a density of from 10, 20 or 40 to up to 100, 200 or 500 milligrams per meter, or more.

Protein resistant groups may be hydrophilic head groups or kosmotropes. Examples include but are not limited to oligosaccharides, tri(propyl sulfoxide), hydroxyl, glycerol, phosphorylcholine, tri(sarcosine) (Sarc), N-acetylpiperazine, betaine, carboxybetaine, sulfobetaine, permethylated sorbitol, hexamethylphosphoramide, an intramolecular zwitterion (for example, —CH2N+(CH3)2CH2CH2CH2SO3-) (ZW), and mannitol.

Additional examples of kosmotrope protein resistant head groups include, but are not limited to:
- —(OCH$_2$CH$_2$)$_6$OH;
- —O(Mannitol);
- —C(O)N(CH$_3$)CH$_2$(CH(OCH$_3$))$_4$CH$_2$OCH$_3$;
- —N(CH$_3$)$_3$$^+$Cl$^-$/—SO$_3$—Na$^+$ (1:1);
- —N(CH$_3$)$_2$$^+$CH$_2$CH$_2$SO$_3$$^-$;
- —C(O)Pip(NAc) (Pip=piperazinyl)
- —N(CH$_3$)$_2$$^+$CH$_2$CH$_2$$^-$;
- —O([Glc-α(1,4)-Glc-β(1)$^-$]);
- —C(O)(N(CH$_3$)CH$_2$C(O))$_3$N(CH$_3$)$_2$;
- —N(CH$_3$)$_2$$^+$CH$_2$CH$_2$CH$_2$SO$_3$$^-$;
- —C(O)N(CH$_3$)CH$_2$CH$_2$N(CH$_3$)P(O)(N(CH$_3$)$_2$)$_2$; and
- —(S(O)CH$_2$CH$_2$CH$_2$)$_3$S(O)CH$_3$.

See, e.g., R. Kane et al., Langmuir 19, 2388-91 (2003) (e.g., Table 1).

In some embodiments, a suitable protein resistant head group comprises poly(ethylene glycol) (PEG), for example PEG of from 3 to 20 monomeric units.

Prior to deposition of further components onto the polymer layer, the substrate with the optional linking layer and polymer layer may be dry or at least macroscopically dry (that is, dry to the touch or dry to visual inspection, but retaining bound water or water of hydration in the polymer layer). For example, to enhance immobilization of a capture agent, the polymer layer may suitably retain bound water or water of hydration, but not bulk surface water. If the substrate with the linking layer and polymer layer has been stored in desiccated form, bound water or water of hydration can be reintroduced by quickly exposing the polymer layer to water (e.g., by dipping in to water) and subsequently blow-drying the surface (e.g., with a nitrogen or argon jet). Alternatively, bound water or water of hydration can be reintroduced by exposing the polymer layer to ambient air for a time sufficient for atmospheric water to bind to the polymer layer.

Capture Region

The device comprises at least one capture region comprising at least one capture agent, which may be non-covalently bound to the polymer layer. The number of capture regions can vary widely and can depend on several factors including the size and shape of the substrate, the intended use of the device (e.g., a point-of-care diagnostic, a panel array (e.g., microarrays for screening DNA, MMChips (microRNAs), protein, tissue, cellular, chemical compounds, antibody, carbohydrate, etc.), and the like. The capture agent comprising a capture region is generally one member of a specific binding pair. Examples of suitable capture agents include, but are not limited to, antigens, antibodies, peptides, proteins, nucleic acids, nucleic acid or peptide aptamers, ligands, receptors, and the like. Embodiments relate to a device comprising a plurality of capture regions that can comprise a plurality of different capture agents such as, for example, a diagnostic panel array.

In embodiments, the capture agent can comprise a biomarker associated with any disease, disorder, or biological state of interest. Accordingly, the selection of the capture agent can be driven by the intended use or application of the device and methods described herein and can include any molecule known to be associated with a disease, disorder, or biological state of interest, or any molecule suspected of being associated with a disease, disorder, or biological state of interest. Thus, the selection of a capture agent is within the ability of one skilled in the art, based on the available knowledge in the art.

In some embodiments, the capture agent can comprise a biomarker associated with any microbial infection of interest, examples of which include but are not limited to: Anthrax, Avian influenza, Botulism, Buffalopox, Chikungunya, Cholera, Coccidioidomycosis, Creutzfeldt-Jakob disease, Crimean-Congo haemorrhagic fever, Dengue fever, Dengue haemorrhagic fever, Diphtheria, Ebola haemorrhagic fever, Ehec (*E. Coli* 0157), Encephalitis, Saint-Louis, Enterohaemorrhagic *Escherischia coli* infection Enterovirus, Foodborne disease, Haemorrhagic fever with renal syndrome, Hantavirus pulmonary syndrome, Hepatitis, Human Immunodeficiency Virus (HIV), Influenza, Japanese encephalitis, Lassa fever, Legionellosis, Leishmaniasis, Leptospirosis, Listeriosis, Louseborne typhus, Malaria, Marburg haemorrhagic fever, Measles, Meningococcal disease, Monkeypox, Myocarditis Nipah virus, O'Nyong-Nyong fever, Pertussis, Plague, Poliomyelitis, Rabies, Relapsing fever, Rift Valley fever, Severe acute respiratory syndrome (SARS), Shigellosis, Smallpox vaccine—accidental exposure, Staphylococcal food intoxication, Syphilis, Tularaemia, Typhoid fever, West Nile virus, Yellow fever, etc.

The capture agent can be deposited on the polymer layer by any suitable technique such as microprinting or microstamping, including piezoelectric or other forms of non-contact printing and direct contact quill printing. When the capture agent is printed on to the polymer layer, it may suitably be absorbed into the polymer layer such that it remains bound when the device is exposed to a fluid, such as a biological fluid. The brush polymer may also provide a protective environment, such that the capture agent remains stable when the device is stored. For example, in embodiments in which the capture agent is a peptide or protein, such as an antigenic protein or an antibody, a brush polymer layer may protect the capture agent against degradation, allowing the device to be stored under ambient conditions.

When an array is formed by the deposition of multiple capture agents at discrete locations on the polymer layer, probe densities of 1, 3, 5, 10, 100 or up to 1000 probe locations per cm$^2$ can be made. Modern non-contact arrayers can be used in the deposition step to produce arrays having up to 1,000,000 probe locations per cm$^2$. For example, using dip-pen nanolithography, arrays with up to 1 billion discrete probe locations per cm$^2$ can be prepared. It will be appreciated that the specific molecular species at each capture spot can be different, or some can be the same (e.g., to provide some redundancy or control), depending upon the particular application, as described herein.

The capture agent may be printed onto the polymer layer to form the capture region. The capture region(s) can be arranged in any particular manner and can comprise any desirable shape or pattern such as, for example, spots (e.g., of any general geometric shape), lines, or other suitable patterns that allow for identification of the capture region on the surface of the polymer and substrate. In embodiments, a plurality of capture agents can be arranged in a predetermined pattern such that the identity of the capture agent is associated with a specific location on the substrate.

Labile Region

The device additionally comprises at least one labile region comprising at least one detection agent and an excipient. In some embodiments, a capture agent may remain non-covalently bound to the polymer layer (e.g., polymer brush) upon contact with a fluid such as a biological fluid, buffer, or aqueous solvent, while the excipient present in the labile region may absorb in to the polymer brush and block absorption of the detection agent. Accordingly, when exposed to an aqueous fluid such as, for example, a sample comprising a biological fluid, the detection agent may be solubilized and release in to the fluid, and may bind to an analyte of interest. The excipient may also further stabilize the detection agent during storage.

In some embodiments, the detection agent may comprise a compound capable of binding to a second member of a specific binding pair. When solubilized and released in to the sample (e.g., a biological fluid), if the second member of the specific binding pair is present in the fluid, it may bind to the detection agent. The second member may then bind to the capture agent in the capture region of the device. Alternatively, the detection agent may encounter the second member of a specific binding pair when already bound to the capture agent. For example, if the capture agent is an antigenic protein and the analyte is a patient-generated antibody that can specifically bind the antigenic protein, the detection agent may comprise an anti-human antibody.

In some embodiments, the labile region may comprise two different agents to form a "sandwich" type assay. In such embodiments, a first agent can bind to the analyte while the other agent binds to the first agent to form a "sandwich" which can then bind to the capture agent. For example, the detection agent may comprise biotin, which may bind avidin or streptavidin that is functionalized with a detection moiety.

The detection agent further comprises a detectable moiety that, directly or indirectly, provides a detectable signal. Exemplary detection moieties include, but are not limited to, fluorophores, chromophores, radiolabels, polynucleotides, small molecules, enzymes, nanoparticles, and upconverters. In some embodiments, the detection moiety may be a fluorophore such as a cyanine (e.g., CyDyes such as Cy3 or Cy5), a fluorescein, a rhodamine, a coumarin, a fluorescent protein or functional fragment thereof, or it may comprise a small molecule such as biotin, or it may comprise gold, silver, or latex particles.

In some embodiments, the excipient is a molecule or a combination of molecules that is selected as to allow for a stable, but non-permanent, association between the detection agent and the polymer. In embodiments the excipient can be partially soluble, substantially soluble or soluble in an aqueous solution (e.g., buffer, water, sample, biological fluid, etc.). In such embodiments, the excipient can be selected from the non-limiting examples of salts, carbohydrates (e.g., sugars, such as glucose, fucose, fructose, maltose and trehalose), polyols (e.g., mannitol, glycerol, ethylene glycol), emulsifiers, water-soluble polymers, and any combination thereof Such excipients are well known in the art and can be selected based on the interaction between the excipient and detection agent, the excipient and the polymer, the solubility of the excipient in a particular medium, and any combination of such factors. In some embodiments the excipient comprises PEG.

The detection agent and the excipient can be deposited on the polymer layer by any suitable technique such as microprinting or microstamping, including piezoelectric or other forms of non-contact printing and direct contact quill printing. A mixture of the detection agent and the excipient may be deposited simultaneously, or the excipient may be deposited prior to the detection agent.

When an array is formed by the deposition of multiple detection agents at discrete locations on the polymer layer, probe densities of 1, 3, 5, 10, 100 or up to 1000 probe locations per $cm^2$ can be made. Modern non-contact arrayers can be used in the deposition step to produce arrays having up to 1,000,000 probe locations per $cm^2$. For example, using dip-pen nanolithography, arrays with up to 1 billion discrete probe locations per $cm^2$ can be prepared. It will be appreciated that the specific molecular species at each capture spot can be different, or some can be the same (e.g., to provide some redundancy or control), depending upon the particular application.

Other Elements

In some embodiments, the device may further comprise an agent to demarcate a patterned region on the polymer layer, such that a fluid (e.g., a biological fluid) will remain confined to a specified region on the polymer layer such that it contacts the capture region and the labile region. Such an agent may be, for example, a hydrophobic ink printed on the polymer layer prior to the deposition of the capture agent and the components of the labile region. Alternatively, the agent may be a wax. In other embodiments, the sample may be contained or directed on the device through selection of an appropriate geometry and/or architecture for the substrate, for example, a geometry that allows the sample to diffuse to the regions comprising the capture agent and the components of the labile spot. In some embodiments the substrate may comprise a well, or a series of interconnected wells.

In some embodiments, for example when the biological fluid is a blood sample, the labile region may comprise an anticoagulant to prevent the blood from clotting. Exemplary anticoagulants include but are not limited to vitamin K antagonists such as coumadin, heparins, and low molecular weight heparins.

In some embodiments, the device may further comprise regions printed with control agents. For example, when the detection agent comprises an anti-human antibody, control capture regions of human IgG may be printed alongside the capture regions to verify the activity of the anti-human detection antibody and to normalize the signal from the detection moiety, such as fluorescence intensities.

Device Storage

After deposition of the capture agent, detection agent, excipient and other optional components, the device is optionally dried, e.g., by mild desiccation, blow drying, lyophilization, or exposure to ambient air at ambient temperature, for a time sufficient for the article to be dry or at least macroscopically dry as described above. Once the device is dry or at least macroscopically dry, it may be sealed in a container (e.g., such as an impermeable or semipermeable polymeric container) in which it can be stored and shipped to a user. Once scaled in a container, the device may have, in some embodiments, a shelf life of at least 2 to 4 months, or up to 6 months or more, when stored at a temperature of 25° C. (e.g., without loss of more than 20, 30 or 50 percent of binding activity).

Detection

Following exposure of a device described herein to a biological sample (e.g., a biological fluid), a signal from the detection agent may be detected using any suitable method known in the art. Exemplary methods include, but are not limited to, visual detection, fluorescence detection (e.g., fluorescence microscopy), scintillation counting, surface plasmon resonance, ellipsometry, atomic force microscopy, surface acoustic wave device detection, autoradiography, and chemiluminescence. As one of skill in the art will appreciate, the choice of detection method will depend on the specific detection agent employed.

Kits

In some embodiments, the disclosure also provides a kit for use in a method described herein. A kit may include a device as described herein, and optionally additional components such as buffers, reagents, and instructions for carrying out the methods described herein. The choice of buffers and reagents will depend on the particular application, e.g., setting of the assay (point-of-care, research, clinical), analyte(s) to be assayed, the detection moiety used, etc. For example, if the capture agent is a polynucleotide and the analyte of interest is a complementary polynucleotide, the kit may include a lysis buffer to be added to the sample of biological fluid, to make the polynucleotide from the sample available for binding.

The kit may also include informational material, which may be descriptive, instructional, marketing or other material that relates to the methods described herein and/or the use of the devices for the methods described herein. In embodiments, the informational material can include information about production of the device, physical properties of the device, date of expiration, batch or production site information, and so forth.

Exemplary Assay Design

The following paragraphs describe one non-limiting embodiment of the disclosure in more detail.

In some embodiments, the disclosure provides a disposable chip that allows for miniaturized, multiplexed assays that can test a biological fluid for one or more IDs of interest. In some embodiments, the assays can be conducted in one step. In certain embodiments, the assays can be conducted without the need for preprocessing or microfluidics. In addition to stable capture spots to bind biomarkers of interest, the devices also include labile microspots that allow secondary detection agents to be printed alongside capture agents. Upon contact with a droplet of a biological fluid, these secondary reagents in the labile spots may dissolve into solution and label a target present in the sample.

Figure 2:
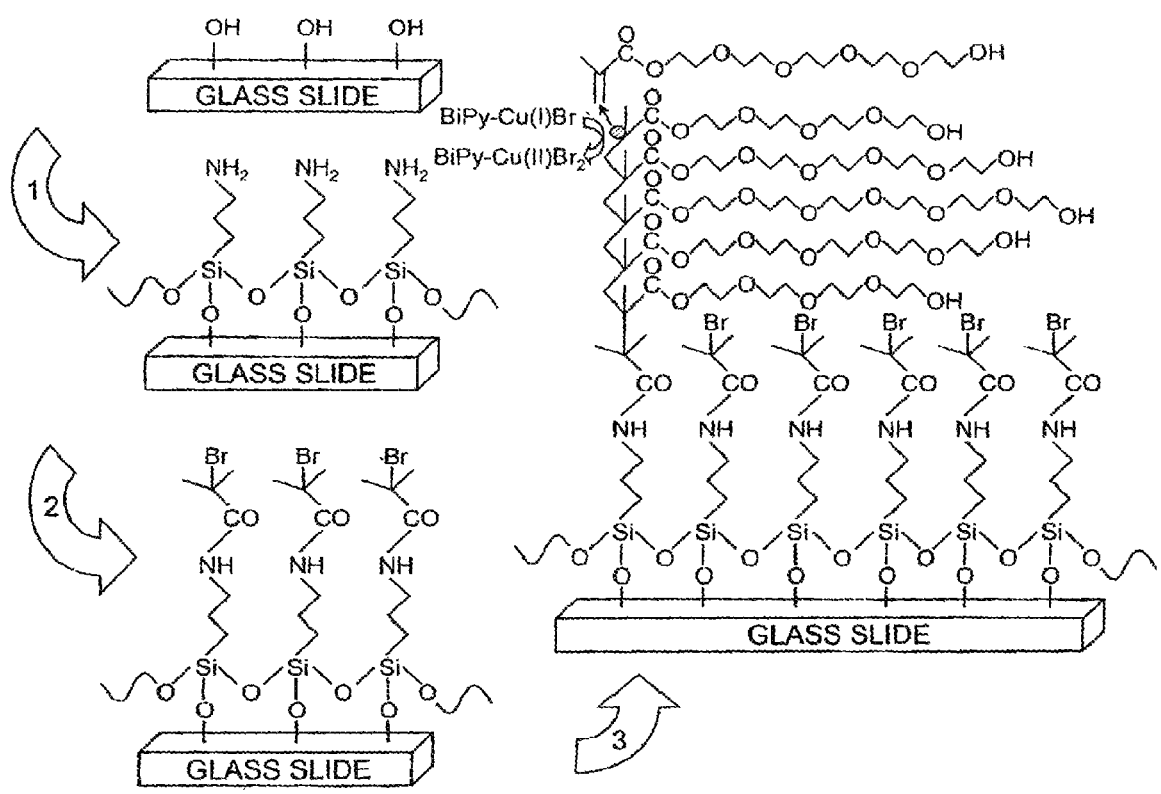
FIG. 2 depicts the synthesis of a POEGMA polymer layer on a glass slide.

In one embodiment of this technology, and as shown in FIG. 1, an assay according to the disclosure comprises, consists of, or consists essentially of a disposable chip which has been coated with POEGMA and then printed with a hydrophobic ink that demarcates a patterned region of POEGMA. The procedure used to synthesize the POEGMA brushes on a glass substrate is summarized in FIG. 2. The pattern region contains spots of individual capture agents. The hydrophilic nature of the POEGMA brush allows a droplet of blood to diffuse across the entire POEGMA surface while the hydrophobic ink creates a "corral" that can confine the blood droplet to the analysis region. The patterned region of POEGMA also contains "labile spots" which include fluorescently-labeled detection antibodies, and soluble polyethylene glycol.

Figure 3:
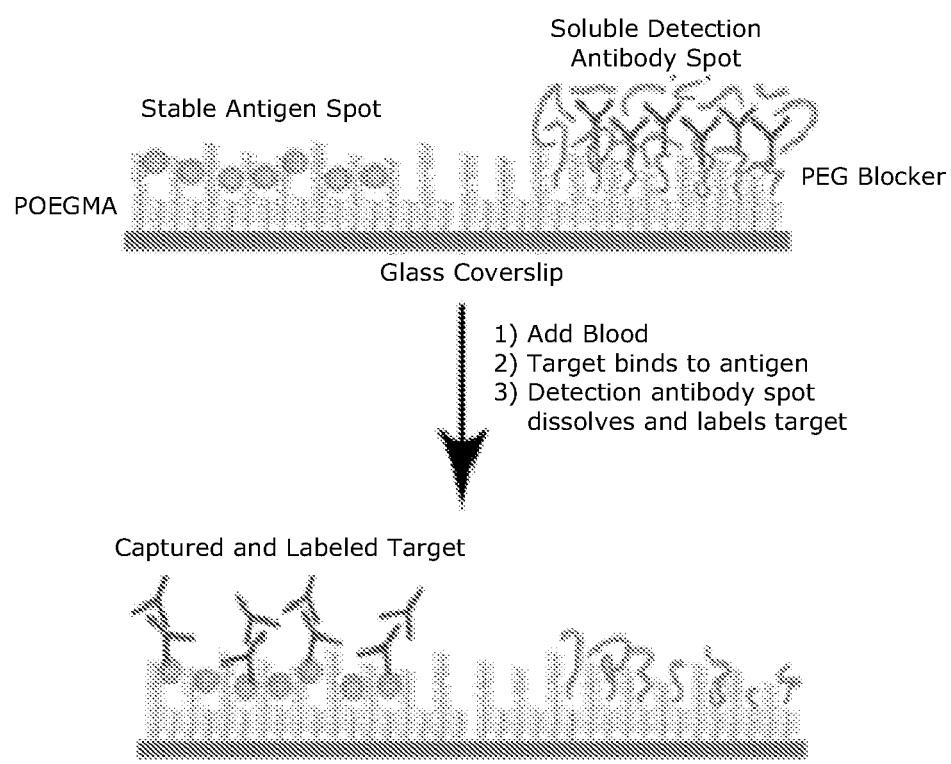
FIG. 3 depicts a cross-section of an exemplary device.

In some embodiments, the capture agents in the capture spots may be antigens that are diagnostic for an TD of interest. When a sample of fluid (e.g., blood) from a patient is applied to the chip, patient-generated antibodies in the sample may bind to the antigen. In such embodiments, the labile spots may include fluorescently-labeled anti-human antibodies that may bind to the immobilized patient-generated antibodies. Such an embodiment of the assay is illustrated in FIG. 3.

Figure 4:
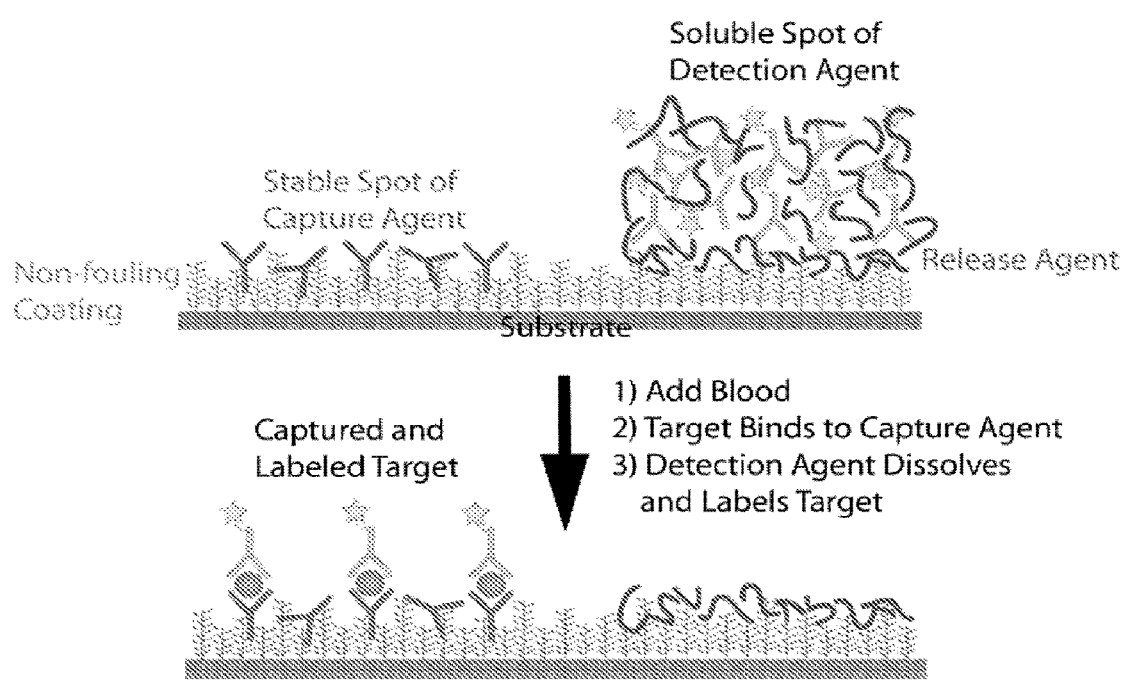
FIG. 4 depicts a cross-section of an exemplary device.

In other embodiments, the capture agents in the capture spots may be antibodies to antigens that are diagnostic for an ID of interest. When a sample of fluid (e.g., blood) from a patient is applied to the chip, patient-generated antigens in the sample may bind to the antibody. In such embodiments, the labile spots may include fluorescently-labeled antibodies that are specific for a different epitope on the same antigen, which may bind to the immobilized patient-generated antigen. Such an embodiment of the assay is illustrated in FIG. 4.

In certain embodiments, the antigenic proteins or antibodies to be used as capture agents are spotted on the POEGMA surface as a row of individual spots of each antigen, in order to provide independent replicates and thereby improve robustness of the assay. For example, a microarray containing microspots of varying capture antibody density may allow a much broader range of analyte concentrations to fall within the dynamic range of a given detector, and may thereby eliminate the dilution series of tests usually run of a single sample. Low analyte concentrations may be detected in regions of high capture antibody density, while high analyte concentrations may be detected in regions of low capture antibody density.

Figure 5:
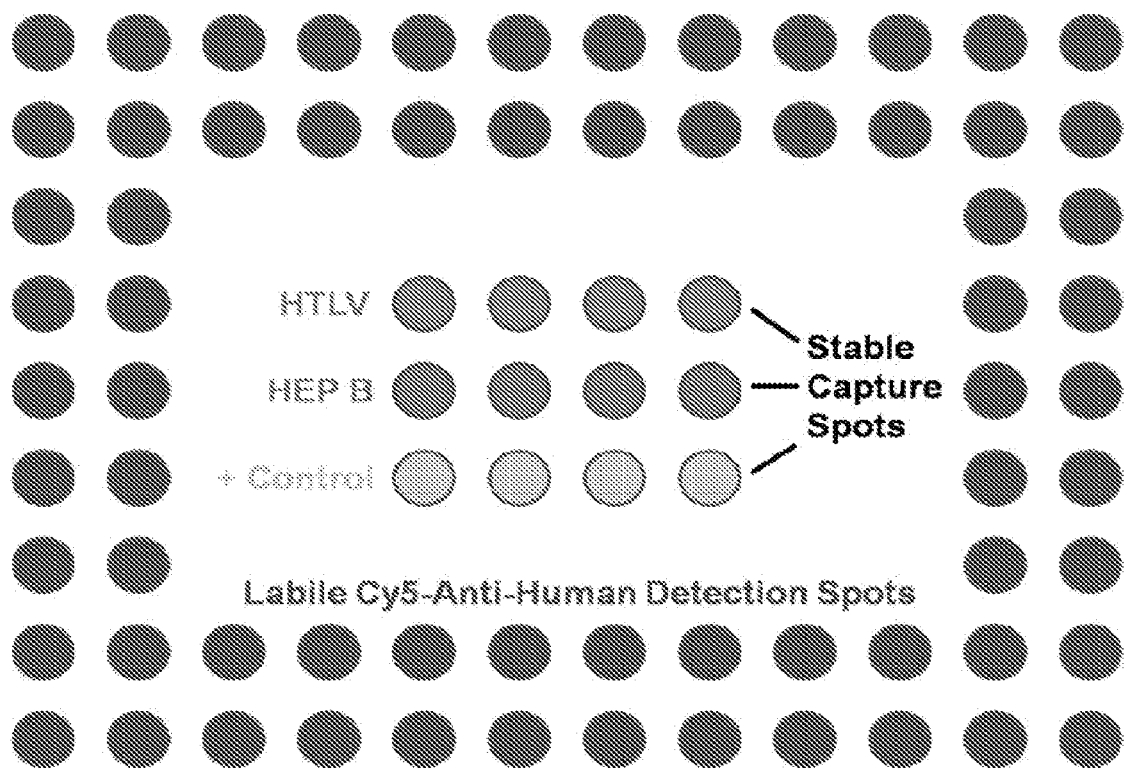
FIG. 5 depicts an exemplary array format.

As depicted in FIG. 5, arrays may be formatted in a manner to ensure that the detection antibody spots are dissolved upon contact with a blood sample. In the figure, twelve separate capture regions are printed as spots, with four spots each of three different capture agents. Labile regions including Cy5-labeled anti-human antibodies as detection agents are printed around the capture spots.

Soluble PEG is also included in the labile spots. The soluble PEG may preferentially absorb into the POEGMA brush and block adsorption of the detection antibody into the brush. Accordingly, the detection antibodies, though confined in spots due to the Piezo inkjet printing and the macroscopic drying process, are in fact in a "labile" state in that they can be easily dissolved and released into the droplet of blood upon contact with an aqueous solution. The addition of excess soluble PEG may also stabilize the fluorescently-labeled detection antibody during storage, and may serve as an excipient that helps resolubilize the detection antibody when the test blood droplet is introduced.

Upon contact with a droplet of blood, the labeled detection antibodies will dissolve into solution. In some embodiments, the detection antibody may be a an anti-human antibody that may bind to, and thereby label, all human antibodies present in the blood sample. Concurrently, the analytes present in the blood, if present, (i.e., patient-generated antibodies against the antigens) may bind to stably printed antigen spots. In other embodiments, the detection antibody may be a specific antibody for an antigen of interest. Upon contact with the blood sample, if the antigen is present in the sample, the detection antibody may bind to the antigen, which in turn may bind to the capture agent antibody.

As positive controls, spots of human IgG may be printed alongside the antigen spots. These will serve to verify activity of the anti-human detection antibody and can also be used to normalize fluorescence intensities across assays to reduce inter-assay variability.

In order to prevent blood clotting, the enzyme heparin may also be printed onto the POEGMA brush in the labile spots. Heparin may be mixed with PEG prior to printing, or may be printed itself in a separate step.

Figure 6:
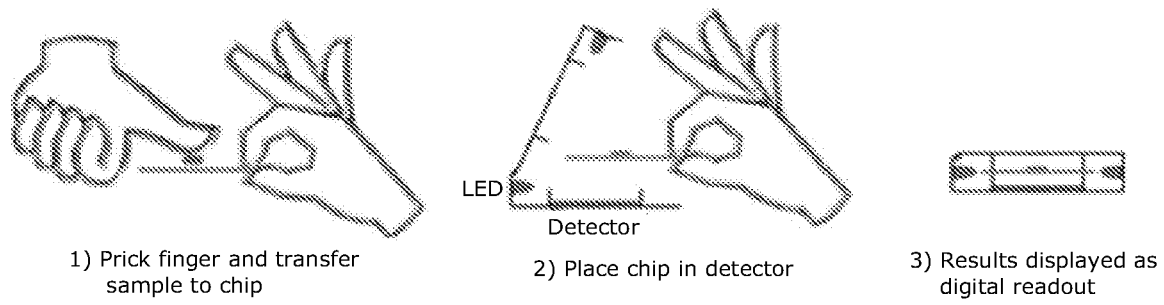
FIG. 6 depicts an exemplary method of using an exemplary device to assay a blood sample from a subject.

In one embodiment, and as shown below in FIG. 6, a finger-stick can be administered to the patient and the resulting droplet of blood applied to the chip surface. The hydrophobic ink printed onto the surface of the chip causes the blood droplet to spread across only the target(s) detection region, where it dissolves to soluble detection agents and heparin (to prevent clotting of blood) printed within the detection region.

As the solubilized, fluorescently labeled detection antibodies are dissolved from their printed spots by the droplet of blood, three serial events must occur to generate a positive signal. These events include the following: (1) binding of the analytes present in blood to the immobilized and non-fluorescent spots of the individual capture agents creates the first half of the sandwich; (2) diffusion of the blood laterally through the polymer brush results in the movement of soluble detection antibodies from their printed spots; (3) upon entering a complex of capture agent and analyte (first half of sandwich), the fluorescently labeled detection antibodies bind to their respective analyte-capture agent spots, completing the sandwich and resulting in the formation of a fluorescent spot at the position where the unlabeled agent had been printed.

In this embodiment the assay is based on supported data that fluorescently labeled detection antibodies that are printed as "labile spots" are carried by flood flow to adjacent rows of printed, and stably immobilized, capture agents by diffusion of the solution containing the analyte. Hence, visualizing the appearance of fluorescence from the spots printed with the different capture agents provides unambiguous identification of different analytes (positives). Quantitation of the concentration of the different analytes is carried out identically to a conventional fluorescence immunoassay by pre-calibrating the device using a dilution series of the analytes spiked into whole blood.

The assay according to this embodiment addresses each of the critical needs in POC testing as follows: (1) the cost of ID testing will be reduced through miniaturization, multiplexing, one-step, on-site processing, and by testing directly in undiluted whole blood obtained from a finger stick with no preprocessing or microfluidics; (2) in order to simplify the ID screening process, diffusion in two-dimensions brings spatially localized reagents together to create a functional assay and thereby eliminating the need for liquid transfer steps, micro-fluidic manipulation of sample or reagents, and wash steps; (3) this multiplexed platform is capable of screening for a panel of ID markers with a single drop of blood with no sample preprocessing; (4) the assay will be fast, which will alleviate the difficulties often associated with communicating the outcome of the ID test; and (5) the actual detection scheme of the disclosed design is a sandwich-type fluorescent immunoassay, which offers the highest sensitivity currently available in the field.

An improvement in ID screening of this magnitude has the potential to substantially affect the health of the entire human population. In order to control infectious diseases, one part of the process is regular screening to identify the various pathogens transmitted through air, food, water, or physical contact, and it is believed that developing the proposed screening platform will make regular and comprehensive ID screening far more accessible to a much larger percentage of the population. Finally, the highly adaptable and modular design is useful in deployment as a diagnostic for many other areas of need as well, including monitoring of biomarkers in clinical trials, pandemic screening, biodefense, and large-scale verification of newly discovered biomarkers.

Methods of ID Screening

The following sections describe several barriers to current methods of ID screening and how each is solved by, for example, the embodiment described above.

Cost

The most accurate immunoassay-based test for a single infectious disease marker is known as the enzyme-linked immunosorbent assay (ELISA) that costs approximately $16 USD and requires on average 6 hours of technician time per marker tested. Recent improvements that enable multiplexing are now capable of testing for an array of four infectious agents at a cost of about $14 USD and requires on average about 4.5 hours of technician time. However, these tests require the use of approximately $110,000-$160,000 USD worth of laboratory equipment. Also, each test required the use of approximately 200 µL of serum or plasma, which must be separated from a sample of whole blood taken from a patient by a venous blood draw. This blood draw is generally taken at the point-of-care and must then be transported to a centralized laboratory for the actual test.

The device according to this embodiment significantly reduces cost by streamlining the key aspects of sample collection, processing and testing as follows: (1) elimination of all preprocessing by directly testing undiluted whole blood obtained from a finger stick; (2) test miniaturization to decrease the amount of reagents—the protein antigens that are spotted as capture agents and the detection antibodies; and (3) one-step, on-site processing. In addition, the test can be multiplexed and capable of targeting a panel of IDs without significantly increasing cost over that of a test for a single ID. This can be achieved without the use of sample preprocessing or the use of microfluidics to separate cells from the analyte solutions because of a unique protein and cell-resistant polymer brush that allows fluoroimmunoassays to be carried out with femtomolar limit-of-detection from whole blood, which is described in further detail herein.

Embodiments providing a multiplexed test create further advantages. Much has been focused on the IDs that receive the greatest media attention, such as HIV, resulting in a general lack of desire or urgency for the general populace to be tested for other IDs. A suitable resolution to this issue is to provide a test for an entire panel of IDs whenever a single ID test is requested, which may result in only incremental cost relative to a test directed to a single ID. Miniaturization of the devices described herein help contain costs because of the vanishingly small, picoliter quantities of the capture reagents and detection antibodies that will be printed in on the devices describe herein. Multiplexing could also help with the discomfort that some people experience when requesting s specific test for a stigmatized disease such as HIV, since it would be one of several IDs found on the chip. Having a multiplexed test that covers many IDs, including food and airborne IDs would allow individuals to feel less apprehensive about requesting testing. In addition, the novel application of engineered functional surfaces (developed by the inventors) allows for the miniaturization of the device to reduce the amounts of capture agent needed, effectively elimination one of the most significant costs in standard laboratory ID screening tests, such as plate-based ELISAs. Furthermore, by employing recently developed techniques of inkjet blotting, disposable, multiplexed sensor chips can be manufactured at a cost on the order of several cents per chip.

Embodiments that reduce the cost of the assay offers several advantages, such as the ability to test more people for less money. But the cost reductions achieved by reducing the required dependence on a highly developed health care infrastructure is also important. For example, traveling clinics in developing nations have limited time and personnel, and a multiplexed test with single-step, on-site processing significantly increases patient throughput and the number of infections detected. In addition, creating a miniaturized, multiplexed assay eliminates vast amounts of materials and significantly reduces the burden of transportation and storage. In particular, the protein-stabilizing property of the current disclosure enables transportation and storage of the chips in ambient temperatures, avoiding the need for costly climate-controlled storage and transport.

Assay Simplicity and Time-To-Readout

People who have experienced an ID test note the anxious waiting period (often days to weeks) leading up to result notification as uncomfortable and a reason for avoiding future tests. More than 50% of patients do not return if a second visit is required to receive test results. Studies have also shown that up to 50% of patients will leave before receiving test results if wait time is 100 minutes, and approximately 20% of patients will leave if wait time is 50 minutes. The devices and methods of the present disclosure eliminate this problem by enabling results within a 5 minute period. This helps ensure that both the test and the result are provided during a single visit, and will eliminate the need for patients to provide contact information for result notification (providing this information can lead to patient privacy concerns, another reason for test avoidance).

Tests requiring whole blood samples drawn by venipuncture require significant effort, time and the availability of highly skilled workers. In addition to the actual drawing of the blood sample, many diagnostics require that the blood be separated into cells and plasma. This required additional equipment and expertise, increased assay cost and time-to-readout, and limits the ability to provide point-of-care diagnosis. Additionally, the process of venipuncture itself can lead to medical complications in the patients, and the strong aversion to that many individuals feel toward needles and venipuncture. All of these concerns can be reduced by creating a test that is capable of detecting a panel of IDs in only a few microliters of blood, which can be easily obtained via a finger-stick. In addition, by creating a test with the ability to detect multiple targets in only a few microliters of blood, increased access for the testing of neonates is possible, where drawing larger quantities of blood is problematic and often requires a blood transfusion at the time of the blood draw due to the quantity of blood required. The devices and methods described herein also have the potential to make a significant impact on the ID screening of newborns, which is often required when either the mother's medical history is unavailable (e.g., in areas of war, famine, and strife), or the potential transmission of a known ID from mother to newborn must be investigated.

Lastly, by relying on diffusion to bring together two spatially separated sets of reagents to generate a signal, the devices and methods described herein eliminate the need for washing or liquid transfer steps. This eliminates the need for expensive or complex microfluidics, which thereby reduces pre-chip cost and eliminates a major cause of failure so common to most contemporary "lab-on-a-chip" designs when they are actually field tested with clinical samples.

Higher throughput of ID testing can be achieved by reducing required materials (e.g., the elimination of needles and blood collection vials, as well as the concern of their proper disposal). In addition, the only disposable item created in the devices and methods of the present disclosure, other than the finger stick lancet, is a small piece of glass or plastic, which serves as the assay's blood contacting surface. Thousands of these could be disinfected with a single liter of bleach solution, and disposal of these surfaces could be in the regular trash. Additionally, testing in low resource settings often occurs in isolated regions. While bringing testing to these areas increases access, it is often the case that any type of follow up is non-existent or occurs only after long periods of time. In addition, face-to-face communication is often the only option, as other methods such as mail, telephone, or email are unavailable or unreliable. For these reasons, rapid results are essential. As mentioned above, options such as lateral flow strip-based tests are available for these situations, but their sensitivity is limited and the potential for multiplexed tests in this format is also limited.

Sensitivity

The devices described in some of the embodiments provide the sensitivity found in standard laboratory tests, such as plate-based ELISA assays, with the advantages of inexpensive, handheld and rapid result lateral flow strip assays. This is achieved by utilizing novel materials in the design of the device (discussed herein in further detail). Through the use of an inexpensive surface coating capable of eliminating the non-specific adsorption of biomolecules and cells. Hence, the devices and methods described herein provide for embodiments that can achieve previously unattainable levels of sensitivity due to the elimination of the largest source of background noise in bioassays that arise from the adventitious adsorption of proteins.

Typically, the most sensitive assays require the support of a technologically sophisticated and capital-intensive healthcare infrastructure. Under current methods, patient samples taken at the point-of-care must be transported to a laboratory that maintains the equipment and personnel required to perform the actual test. Low resource settings simply do not have access to such facilities, which precludes these areas from having access to the most sensitive diagnostics. The device according to some embodiments offers on-site analysis, which allows the highly sensitive diagnostic to be utilized in settings where the healthcare infrastructure is less developed.

One skilled in the art will readily appreciate that the exemplary embodiment disclosed above is well adapted to carry out the objects and obtain the ends and advantages mentioned, as well as those inherent therein. The methods, procedures, treatments, molecules, and specific compounds described in this embodiment are merely representative of one contemplated application of the more general technology, and should not be considered to be limiting to the aspects and embodiments disclosed more generally above.

The following non-limiting Examples are intended to be purely illustrative, and show specific experiments that were carried out in accordance with the disclosure.

EXAMPLES

Example 1. Synthesis of POEGMA Brushes on Glass Slides

The POEGMA brushes were fabricated on glass as follows (FIG. 2, all chemicals purchased from Sigma): first, glass slides (VWR) were cleaned in a solution of 3:1 $H_2SO_4:H_2O_2$ for 30 minutes. After rinsing with deionized $H_2O$ and drying, the cleaned slides were immersed in 10% aminopropyltriethoxysilane (APTES) in ethanol for 30 min and were then rinsed with ethanol and dried at 120° C. for 3 h (step 1). Slides were then immersed in a solution of 1% bromoisobutyryl bromide and 1% triethylamine in dichloromethane for 30 min, rinsed with dichloromethane and ethanol, and blown dry with $N_2$ (step 2). Slides were then immersed for 12 h in a degassed polymerization solution of 5 mg/mL Cu(I)Br, 12 mg/mL bipyridine and 300 mg/mL oligo(ethylene glycol) methacrylate under argon (step 3). Finally, slides were rinsed with deionized $H_2O$ and blown dry with $N_2$.

Example 2. Protein Resistance of POEGMA Brushes

Figure 7:
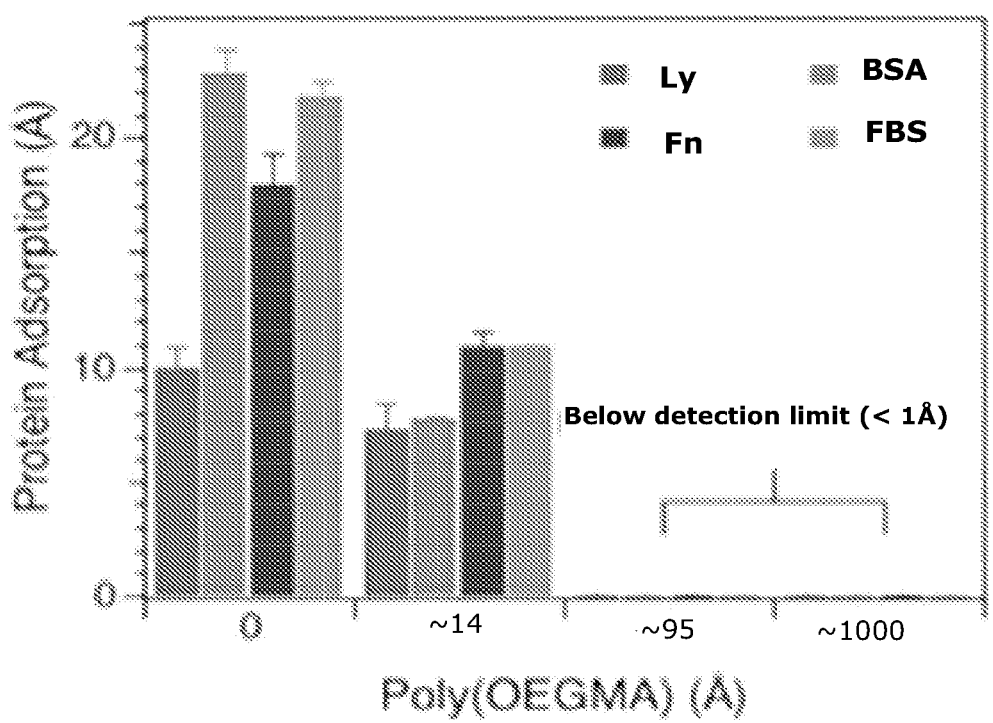
FIG. 7 depicts protein adsorption on POEGMA brushes of different thicknesses on silicon oxide and initiator-silane modified silicon oxide (control: 0) measured by ellipsometry. Legend: Ly (lysozyme), Fn (fibronectin), BSA (bovine serum albumin), FBS (fetal bovine serum).

The protein resistance of the POEGMA brushes grown on silicon wafers was tested by adsorption of fibronectin (Fn), bovine serum albumin (BSA), lysozyme (Ly) (all proteins at 1 mg/mL in PBS, pH=7.4), and undiluted fetal bovine serum (FBS). The thickness of the protein layers as a function of the POEGMA film thickness was measured by ellipsometry, and is shown in FIG. 7. The thickness of the adsorbed protein on the negative control—a surface with immobilized ATRP initiator—varied depending upon the protein, and ranged from ~10 Å (Ly) to ~25 Å for the other proteins and FBS. In contrast, a thin POEGMA brush ~14 Å thickness) showed significantly less protein adsorption of all proteins and of serum. Increasing the thickness of the POEGMA brush to ~95 Å or greater eliminated the adsorption of all proteins, and most notably that of serum proteins, to below the 1 Å detection limit of ellipsometry.

Example 3. Printing of Antibody Microarrays

A non-contact PerkinElmer Piezorray was used to print Ab microarrays onto POEGMA substrates at room temperature and humidity. Antibodies for IL-6 and Osteoprotegerin (OPG) (R&D Systems) were printed from 50 μg/mL solutions and allowed to non-covalently absorb into the 100 nm thick polymer brush: (1) a 100 nm thick POEGMA brush grown by SI-ATRP on glass, and (2) on unmodified nitrocellulose substrates (Whatman, positive control). After printing, drying of the spots was facilitated by placing the printed slides under vacuum.

Arrays were first incubated with a dilution series of 100 mL of analyte-spiked PBS or serum for 2 h with stirring, followed by 100 ml 1 mg/ml biotinylated secondary antibody in PBS with 1% (w/v) BSA for 1 h. Finally, the arrays were developed by incubation in 100 mL of 1 μg/ml streptavidin-Cy5 for 30 min, and then scanned with an Axon Genepix 4200 fluorescence microarray scanner. After each incubation step, arrays were washed twice for 30 s with 1% BSA (w/v) and 0.1% (w/v) Tween-20 in PBS.

Figure 8A:
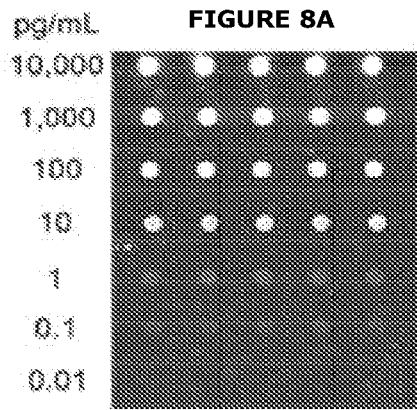
FIG. 8A depicts image of an IL-6 microarray interrogated from serum.
Figure 8B:
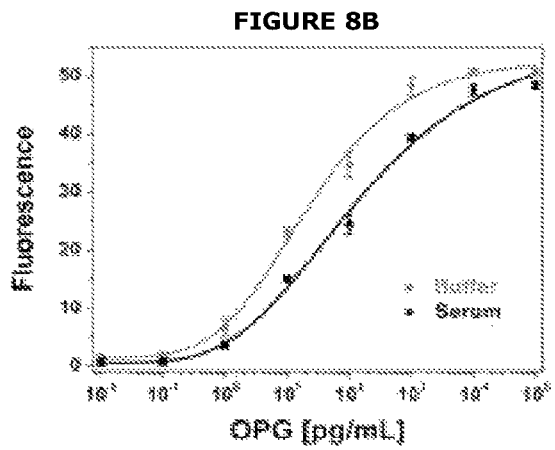
FIG. 8B depicts dose response curves of OPG in buffer and serum on poly(OEGMA).
Figure 8C:
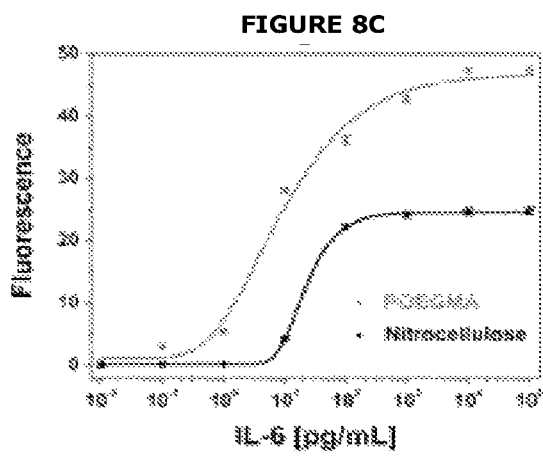
FIG. 8C depicts dose response curves of IL-6 in serum on poly(OEGMA) and nitrocellulose.
Figure 8D:
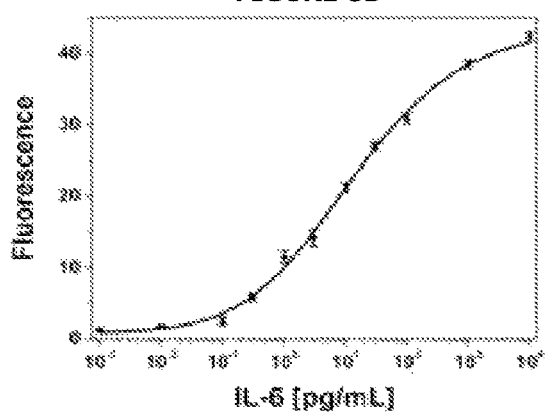
FIG. 8D depicts dose response curve for an IL-6 microarray interrogated from whole blood.

A fluorescence image of microarray spots for an IL-6 assay spotted on POEGMA on glass, shown in FIG. 8A, shows the increase in fluorescence intensity with increasing analyte concentration. Spots could be visually discriminated from background even at an IL-6 concentration of 0.1 pg/mL (5 tM). FIG. 8A also shows that the POEGMA matrix retained its ability to resist non-specific protein adsorption throughout array fabrication and the subsequent sandwich immunofluorescence assay, as the fluorescence intensity in the background areas surrounding spots measured prior to the assay showed no increase in intensity upon completion of the procedure. This background signal on POEGMA translates to femtomolar limits of detection (LODs) in serum, and a dynamic range that spans five orders of magnitude of analyte concentration (FIG. 8B through 8D). Furthermore, despite the incubation and rinse steps, there was no bleeding of the spots (FIG. 8A), which confirmed the stable immobilization of the capture antibody.

The OPG dose response curves in buffer and serum for OPG-specific antibodies spotted on POEGMA (FIG. 8B) illustrates another important consequence of the use of a protein resistant substrate, as they show that the LODs are virtually identical in buffer and serum. These results are in contrast to most other fluorescence immunoassays, where the LOD is typically orders of magnitude greater in complex physiological solutions containing high concentrations of extraneous proteins compared to the LOD for the same the assay in buffer. Although the absolute signal from the spotted arrays on POEGMA was lower than that obtained from arrays spotted on nitrocellulose (raw data not shown), the background signal obtained from the POEGMA brush (which approached the autofluorescence levels of the glass substrate) was significantly lower than that from nitrocellulose. The fluorescence response of an IL-6 specific antibody array spotted on nitrocellulose and POEGMA as a function of IL-6 concentration in serum are shown in FIG. 8C. The data show that the fluorescence signal from the printed capture Ab spots on nitrocellulose are only visible to a concentration of 10 pg/ml, while the signal on POEGMA is clearly visible down to a concentration of 100 fg/ml. Despite the lower absolute signal from the antibody arrays spotted on the POEGMA brush versus nitrocellulose, the significantly lower background fluorescence on the POEGMA brush more than compensated for the lower absolute signal from the spots. Additionally, antibodies to IL-6 spotted on a POEGMA brush on glass could detect IL-6 directly from undiluted, whole blood with a LOD of ~15 fM (FIG. 8D).

Example 4. Dose Response of Printed Antibody Microarrays

Two different concentrations of biotinylated antibody (b-Ab) were used to create a microarray on POEGMA brush surfaces, which were then exposed to a dilution series of streptavidin-Cy5 (FIG. 9A). The concentration of the printed solutions varied by 4 orders of magnitude (1 mg/mL b-Ab and 0.0001 mg/mL b-Ab). The dose response of these microarrays to streptavidin was obtained by exposing the arrays to known concentrations of Cy5 labeled streptavidin (FIG. 9B). Spots with a high b-Ab concentration exhibited a dynamic range of six orders of magnitude, from 4 fM to 4 nM. Spots with a low b-Ab concentration also had a dynamic range of six orders of magnitude, from 1 pM to 1 μM, and proved to be useful for quantifying the higher concentrations of Cy-5 streptavidin that generated detector-saturating signal in the spots of high b-Ab concentration. By combining the response of both spot concentrations, a response of 9 orders of magnitude was obtained.

Figure 10:
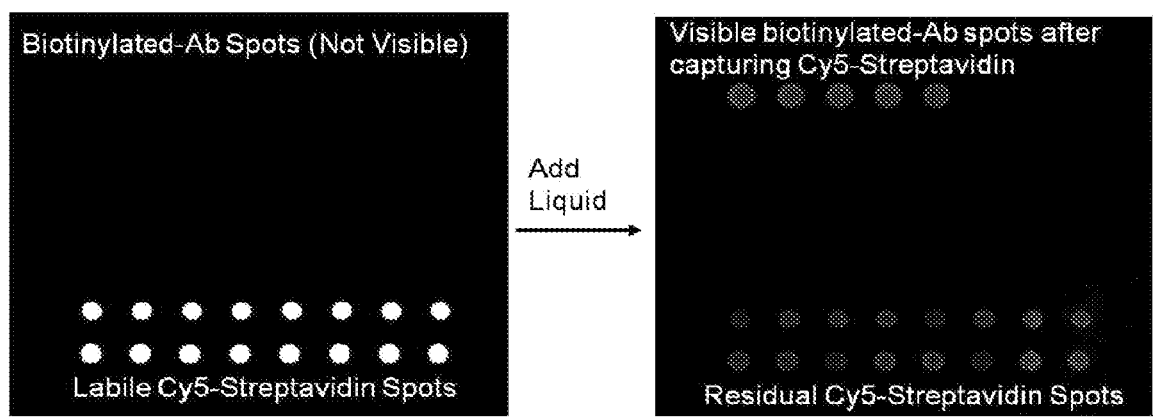
FIG. 10 depicts fluorescence images of an exemplary chip printed with b-Ab capture spots and Cy5-streptavidin labile spots, before and after addition of a drop of buffer.

Example 5. Printing of Stable b-Ab Capture Spots and Streptavidin-Cy5 Labile Spots An array of five biotinylated-Ab spots were printed onto a POEGMA surface to form the "stable" immobile spots of the capture agent. In addition, a solution of streptavidin-Cy5 and soluble PEG was spotted on top of pre-printed spots of soluble PEG to create an 8×2 array of "labile" spots of detection reagents. The device is shown in FIG. 10, where the stable spots cannot be seen in the top part of the left panel because they are not fluorescent. After one week of storage, 50 μL of PBS was was pipetted on to the surface of the array to test the ability of the streptavidin-Cy5 spots to dissolve into solution and bind to the biotinylated-Ab capture spots. As shown in FIG. 10, a sufficient amount of active Cy5-streptavidin was dissolved into solution and captured by the biotinylated-Ab spots to create a detectable signal.

Example 6. Dose Response of a BNP Assay

Figure 11:
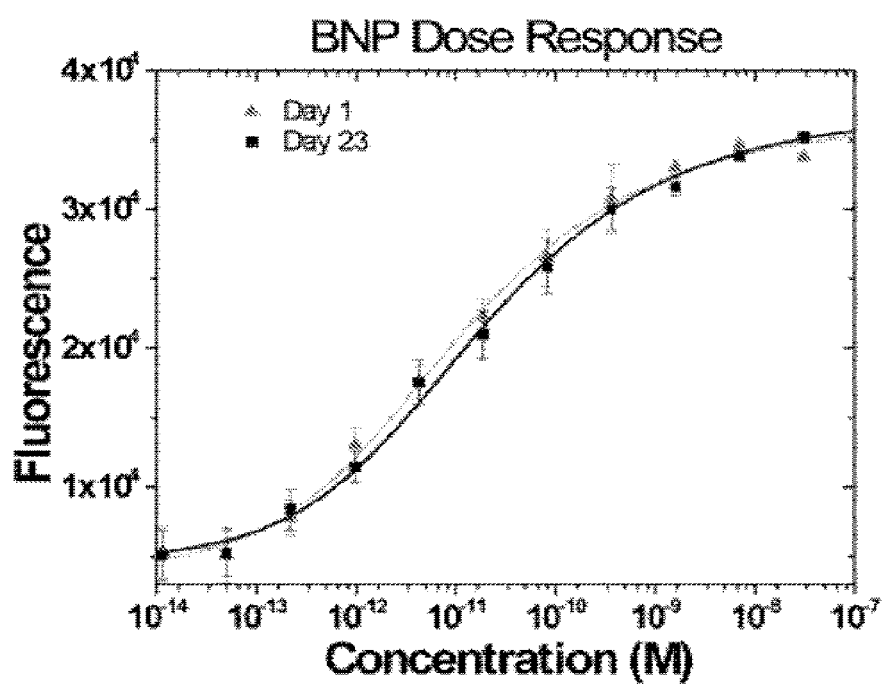
FIG. 11 depicts a dose-response curve for an assay for BNP detection after 1 day of RT storage after printing (gray triangles) and 23 days of storage after printing (black circles).
Figure 14:
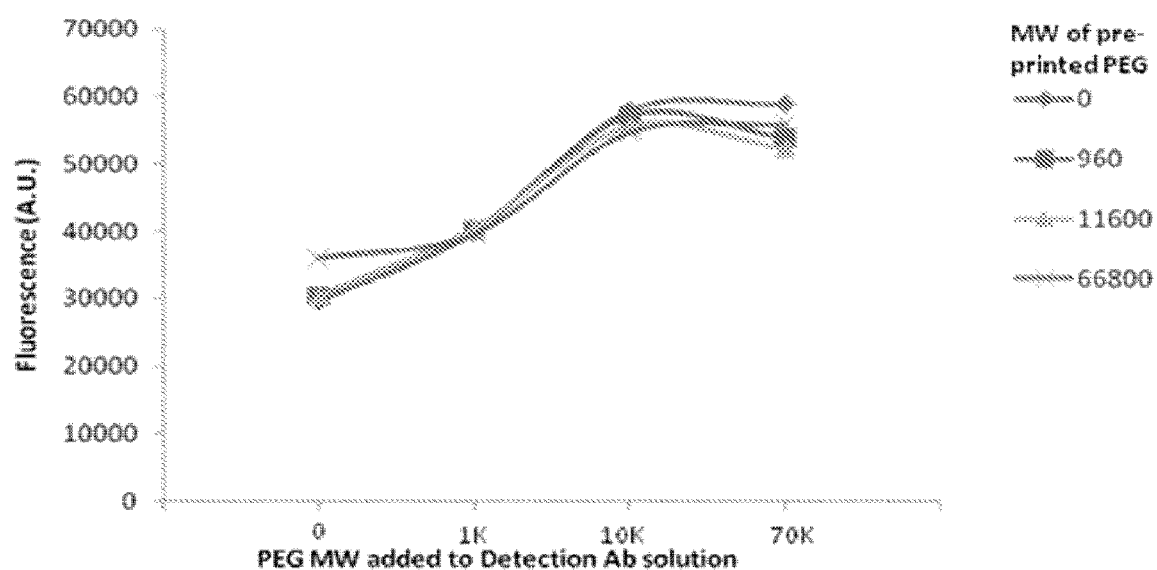
FIG. 14 depicts captured fluorescence from an assay in which varying molecular weights of PEG were pre-printed on the polymer layer, and/or included with the capture agent solution.

The dose response of an assay printed on POEGMA for detection of brain naturietic peptide (BNP), a biomarker for cardiac injury, were measured after 1 day of storage at room temperature (RT) and after 23 days of storage. This assay was performed to determine: (1) quantification possible with the assays and (2) their stability following storage. The analyte was incubated for 20 min to simulate POC testing conditions. The data was fit with a 5-parameter logistic fit, and yielded a LOD of 8 pg/ml as shown in FIG. 11; the i-Stat test (Abbott) has an LOD of 14 pg/mL in comparison. Importantly, there is no difference in the LOD or DR of the assay, even after storage for 3 weeks. These results are also consistent with previous observations of other investigators that PEG can stabilize proteins under ambient conditions. The long shelf-life under ambient conditions is an important attribute for point-of-care devices because these printed diagnostic devices will not need to be stored in buffer at 4° C., so that the printed chips can be transported, stored and used at room temperature, attributes that are important for use in low-resource settings where refrigeration may not be easily available.

Example 7. Assay to Detect Human IgGs and IgMs

In this example an assay to detect human IgGs and IgMs from blood was prepared. These analytes were chosen because healthy donor blood can be used for this purpose. FIGS. 12A and 12B show the fabrication of the assay. First a ~100 nm thick POEGMA brush was grown on a glass slide by SI-ATRP. Then the glass slide was stamped with a grid pattern of wax using a slide imprinter to confine the sample to the active area of this chip. An antibody array was next inkjet printed in the center of a single wax corral; each spot is ~150 μm in diameter. The inner 4×4 array are spots of capture Abs (Abes) to form the "stable" capture spots; rows 1 and 4 are an anti-murine Abe (positive control); row 2: anti-human IgG Abe; row 3: anti-human IgM Abe. Next, the detection cocktail was printed as 3 outer rows of "labile" spots (FIG. 12B). These spots contain a mixture of murine Cy-5-anti-human-IgG and/or murine Cy-5-anti-human-IgM (detection Ab's with a different epitope against human IgG and IgM than the $Ab_c$s), heparin, and 10×-molar excess PEG5000. The inner 4×4 antibody array has no intrinsic fluorescence and is only barely visible in FIG. 12B because of light scattering from the printed Ab's. The outer spots are visible because they contain Cy5-labeled Abd's at a high enough concentration that they saturate the fluorescence detector and hence appear white.

A drop of blood from a finger stick (~20 μL) was applied to the surface of the assay within the hydrophobic corral, and incubated for 5 min. The surface was quickly rinsed with ~1 ml buffer from a squeeze bottle, which should displace the loosely bound blood cells and proteins. The blood flowed to the margins and bound to the hydrophobic corrals, manifesting as a red color around the margins (not shown). FIGS. 13A-13F illustrate the results of the assay. In FIG. 13B, Abds for human IgG and IgM were co-printed as the labile detection spots (with PEG+heparin), so that a complete sandwich is created upon incubation in blood, leading to fluorescent spots appearing in both rows 2 and 3. The margin signals in FIGS. 13B-13F are due to scattering from the blood bound to the hydrophobic corral after displacement from the POEGMA brush by the wash step. In whole blood, the concentration of IgG is roughly 5 mg/mL (33 μM) and that of IgMs 1.5 mg/mL (1.6 μM), suggesting that these protein analytes should be detected from undiluted blood at this level even in this initial experiment. FIGS. 13C and 13F show negative control experiments in which the chip was incubated with either PBS (C) or chicken blood (F), so that only the positive controls: rows 1 and 4 light up, while rows 2 and 3 show no fluorescence. FIGS. 13D and 13E are two other controls; in FIG. 13D, only the Cy5-anti-IgG $Ab_d$ was printed in the labile spots, so that row 2 lights up but row 3 does not, while in panel 13E, only the Cy5-anti-IgM $Ab_d$ was printed in the labile spots, so that row 3 lights up, while row 2 does not. Note that the Cy5-$Ab_d$s were printed at high concentrations in the outer circumference of labile spots, and are only partially dissolved upon contact with blood, so that their residual fluorescence still saturates the detector.

Example 8. Evaluation of Excipient Printing Mode

Two approaches were evaluated for their effect on dissolution of printed capture agent antibodies ($Ab_d$): (1) Soluble PEG added to the print solution of the $Ab_d$, and (2) Soluble PEG that is pre-printed directly into the POEGMA brush prior to printing of the Abd.

Three molecular weights of PEG were evaluated: 1000, 11000, and 66000 Da. Each of these PEGs were added to the print solution of a Cy-5 labeled cardiac troponin I (cTnI) antibody at a concentration of 1 mg/mL. Soluble PEG at a concentration of 1 mg/mL was also printed on to the POEGMA brush prior to printing the detection agent on top of these spots of PEG. After printing microspots of soluble PEG, Abd microspots were printed directly on top of the previously printed PEG. To determine the effectiveness of adding PEG to the print solution, spots of Abd were printed around an array of cTnI $Ab_c$ spots. 20 μL of buffer containing cTnI was added to the array, which allowed the Cy-5 anti-cTnI antibody spots to dissolve into solution, and label the cTnI.

Upon scanning, the signal generated by the stable Abe spots after capture of labeled cTnI was determined. PEG of MW 10000 or 66000 added to printed detection antibody solution improved detection antibody availability. Pre-printing PEG did not appear to greatly affect detection antibody availability.

Example 9. Single Analyte and Multiplexed Sandwich Assays for HBV and HIV

A microarray comprising of a disposable chip coated with POEGMA will be prepared, whose boundaries will then be printed with a hydrophobic hydrocarbon ink with a microarray slide imprinter (ArrayIt Corp.). The hydrophobic ink will create a "corral" that will confine the blood droplet to the active region of the chip. For the single analyte assay, this active region will be printed "stable" spots of individual $Ab_c$ that are specific for Hepatitis B Surface Antigen (HBsAg). A row of HBsAg will be printed to serve as a positive control. F or the multiplexed D4 assay, p24 and gp41 (for HIV-1), and gp36 (for HIV-2) will also be printed in separate rows, and spots of the HIV antigens will be printed alongside the capture antibody spots as a positive control. The $Ab_c$ will be spotted on the POEGMA surface as a row of individual spots in order to provide independent replicates and thereby improve the statistics of detection and the robustness of the assay. The hydrophilic nature and architecture of the POEGMA brush will allow a droplet of blood to diffuse across the active POEGMA region of the chip.

In addition to the "stable" spots of the capture Abs, soluble-labile" spots of fluorescently labeled detection antibodies (Abd) will also be printed. Arrays will be formatted in a manner similar to that shown in FIG. 5. To ensure that the labile spots of printed $Ab_d$ are dissolved upon contact with blood, soluble PEG will be added to the print solutions. This soluble PEG will preferentially adsorb into the POEGMA brush and block adsorption of the Abd into the brush. Although confined in spots simply due to the inkjet printing and the macroscopic drying process, these Abd are in fact in a "labile" state and can be easily dissolved and released upon contact with an aqueous solution. The addition of excess soluble PEG to the detection Ab will serve to stabilize the detection agents during storage, and importantly serves as an excipient that helps resolubilize the detection Ab when the test blood droplet is introduced. Upon contact with a droplet of blood, these labeled antibodies will dissolve into solution and bind to, and thereby label, all target present in the blood sample. As a positive control, spots of the HBV and HIV antigens will be printed alongside the capture antibody spots. These will serve to verify activity of the detection agents, and can also be used to normalize fluorescence intensities across assays to reduce inter-assay variability. In order to prevent clotting, labile heparin spots, similarly mixed with excess PEG, will also be printed on the brush.

Example 10. Self-Contained Assay Capable of Detecting Multiple Infectious Markers Directly in Whole Blood In this example, a quantitative single analyte assay for HBV and a qualitative multiple analyte D4 assay for HBV and HIV will be developed using detection agents printed as "labile spots" for a POC immunoassay.

Antibody responses useful in detecting HIV infection are generally against three classes of antigenic proteins: envelope antigens (ENV), polymerase gene products (POL), and group-specific antigen (GAG). In general, a single HIV antigen is not adequately sensitive or specific for serodiagnosis, so that a combination of antigens is most useful for serodiagnosis. The primary envelope antigen will be gp41, with gp120, and gp160 as backups. A primary antigen for evaluation from the core proteins is p24 (GAG), with other antigens including p55 (a GAG protein that is the precursor to p24) and p53 (POL). Identification of HIV-2 infection is also important. The leading candidate antigen for HIV-2 is gp36 (ENV), the analogue to HIV-1's gp41.

The diagnosis of HBV is straightforward as the presence of HBsAg in the sample is indicative of infection. Commercially available monoclonal and polyclonal antibodies to HBsAg will be assessed in this platform to determine those most suitable for the platform.

Single Analyte Quantitative Assay. Optimized POEGMA surfaces and detection agent printing conditions, such as those described herein, will be used to print an array of anti-HBsAg microspots (in a format analogous to the array shown in FIG. 5). Five replicate spots of anti-HBsAg Ab will comprise a single row in the array, and a row of HBsAg will also be printed to serve as a positive control. Microspots of a Cy5 labeled anti-HBsAg detection antibody will be printed in the region surrounding the capture antibody and positive control rows. Twenty-four arrays will be printed on one slide, and four slides will be assembled into a 96 well plate format. Dose-response curves covering concentrations from 0 g/mL to 100 ng/mL will be generated using target spiked buffer, followed by dose-response curves from HBV-negative human blood spiked with the analyte from 1 fM to 1 µM. The dose-response data will be fit to a five-parameter logistic (5-PL) fit. Parameter estimation will be performed by a large-scale trust-region reflexive Newton algorithm using MATLAB (Version 6.5). The assay will be evaluated in terms of its LOD, DR, and COV. For assays with heparinized whole blood (heparinized by dissolution of the detection cocktail), removal of blood from the surface is necessary to image the fluorescence. Hence, different "displacement" protocols to remove blood from surface will be explored: (1) Drop-wise washing of surface using a Visine bottle; (2) insertion of chip into buffer-filled bottle with tracks that guide insertion and immersion of the chip and its removal from bottle. We will first use a Wilhelmy plate balance to insert and withdraw the chip into the buffer at different rates and for different total times of incubation to optimize this protocol. The impact of both blood "displacement" methods on assay LOD, DR, and COV will be determined, and the best protocol will be used for all blood assays.

Multianalyte Qualitative Assay. Optimized POEGMA surfaces and detection agent printing conditions, such as those described herein, will be used to print an array of anti-HBsAg, anti-p24, anti-gp41, and anti-gp36 capture Ab microspots (in a format analogous to the array shown in FIG. 5). Five replicate spots of each capture antibody will comprise a single row in the array, and there will also be one positive control row of each antigen. Microspots composed of a mixture of the necessary Cy5 labeled detection antibodies will be printed in the region surrounding the capture antibody and positive control rows. Dose-response curves will be generated using analyte-spiked buffer, followed by analyte-spiked human blood (HTV/HBV negative) and the data will be fit as described previously for the single analyte assay. The dose-response curve of the single analyte HBsAg will be compared to that obtained from the 4-analyte D4 assay, to examine the effect of simultaneous exposure to multiple analytes and the printing of 4 different detection Abs on the same chip on the performance of the D4 assay in terms of potential cross-reactivity. Further, we note that although these multianalyte assays will be quantitatively characterized in this SA, they will only be used in a qualitative—yes/no format—in SA4 to establish the presence or absence of an analyte, when the signal exceeds the threshold of 3σ LOD, where the LOD is established by the dose-response curve in blood.

All patents, publications and references cited herein are hereby fully incorporated by reference. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

The invention claimed is:

1. A device comprising:
  a. a substrate comprising a surface;
  b. a non-fouling polymer layer on the surface;
  c. a plurality of capture regions on the non-fouling polymer layer, each comprising at least one capture agent; and
  d. a plurality of labile regions on the non-fouling polymer layer, each comprising at least one detection agent and an excipient;
  wherein the plurality of capture regions and the plurality of labile regions are spatially separated, and wherein the non-fouling polymer layer allows a biological fluid to move across the surface by diffusion.

2. The device according to claim 1, wherein the non-fouling polymer layer comprises a plurality of poly(oligo(ethylene glycol)methyl methacrylate) (POEGMA) brush molecules.

3. The device according to claim 1, wherein each of the plurality of capture regions comprises at least two different capture agents.

4. The device according to claim 1, wherein the at least one capture agent in each capture region of the plurality of capture regions is different from the at least one capture agent in other capture regions of the plurality of capture regions.

5. The device according to claim 1, wherein the capture agent is a biomarker, wherein the biomarker comprises a cell, a small molecule ligand, a lipid, a carbohydrate, a polynucleotide, a peptide, a protein, an antigen, or an antibody.

6. The device according to claim 1, wherein the detection agent comprises a small molecule ligand, a lipid, a carbohydrate, a polynucleotide, a peptide, a protein, an antigen, or an antibody.

7. The device according to claim 1, wherein the detection agent comprises a detection moiety selected from the group consisting of a chromophore, fluorophore, a radiolabel, a polynucleotide, a small molecule, an enzyme, a nanoparticle, a microparticle, a quantum dot, or an upconverter.

8. The device according to claim 1, wherein the excipient is selected from the group consisting of a salt, a carbohydrate, a sugar, an emulsifier, a water-soluble polymer, and any combination thereof.

9. The device according to claim 8, wherein the excipient is poly(ethylene glycol).

10. The device according to claim 1, wherein at least one labile region further comprises heparin.

11. The device according to claim 1, wherein the substrate comprises glass, silicon, a metal oxide, or a polymer.

12. The device according to claim 1, further comprising a linking layer between the substrate and the non-fouling polymer layer.

13. The device according to claim 1, further comprising a demarcating agent to demarcate a detection region on the surface or on the non-fouling polymer layer.

14. The device according to claim 13, wherein the demarcating agent is a hydrophobic ink or wax.

15. A method of manufacturing a device according to claim 1, the method comprising:
   a. forming a non-fouling polymer layer on a surface of a substrate;
   b. printing the at least one capture agent onto the non-fouling polymer layer; and
   c. printing the at least one detection agent and the at least one excipient onto the non-fouling polymer layer;
      wherein the at least one capture agent is printed onto the non-fouling polymer layer in a region that is spatially separated from the at least one detection agent and the at least one excipient.

16. A method of detecting a disease, biological state or a disorder in a subject comprising:
   a. contacting a biological fluid obtained from the subject with the device of claim 1 for a time sufficient to allow the at least one detection agent in the labile region to solubilize;
   b. detecting the presence of a detectable signal from the detection agent,
      wherein the presence of a detectable signal on at least one of the plurality of capture regions on the device indicates the presence of the disease, biological state or disorder in the subject.

17. A diagnostic assay for determining a disease, a disorder, or a biological state in a subject comprising:
   a. contacting a biological fluid obtained from the subject with the device of claim 1 for a time sufficient to allow the detection agent in the labile region to solubilize;
   b. detecting the presence of a detectable signal from the detection agent,
      wherein the presence of a detectable signal on at least one of the plurality of capture regions on the device indicates the presence of the disease, disorder, or biological state in the subject.

18. The diagnostic assay of claim 17, wherein the assay is a point-of-care assay.

19. A kit comprising the device according to claim 1, further comprising a set of buffers and/or reagents, and instructions.

20. The device according to claim 1, wherein the biological fluid is selected from the group consisting of blood, serum, plasma, lymph fluid, bile fluid, urine, saliva, mucus, sputum, tears, cerebrospinal fluid (CSF), bronchioalveolar lavage, nasopharyngeal lavage, rectal lavage, vaginal lavage, colonic lavage, nasal lavage, throat lavage, synovial fluid, semen, ascites fluid, pus, maternal milk, ear fluid, sweat, and amniotic fluid.

* * * * *